(12) United States Patent
Kubo et al.

(10) Patent No.: US 10,676,784 B2
(45) Date of Patent: Jun. 9, 2020

US010676784B2

(54) SAMPLE ANALYZING METHOD AND SAMPLE ANALYZER

(71) Applicant: SYSMEX CORPORATION, Kobe-shi, Hyogo (JP)

(72) Inventors: Takuya Kubo, Kobe (JP); Shigeki Iwanaga, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 435 days.

(21) Appl. No.: 15/075,358

(22) Filed: Mar. 21, 2016

(65) Prior Publication Data

US 2016/0281151 A1 Sep. 29, 2016

(30) Foreign Application Priority Data

Mar. 27, 2015 (JP) ................................ 2015-065666

(51) Int. Cl.
*G01N 21/64* (2006.01)
*C12Q 1/6841* (2018.01)
*G02B 21/00* (2006.01)

(52) U.S. Cl.
CPC ....... *C12Q 1/6841* (2013.01); *G01N 21/6428* (2013.01); *G01N 21/6458* (2013.01); *G01N 2021/6432* (2013.01); *G01N 2021/6441* (2013.01); *G02B 21/0076* (2013.01)

(58) Field of Classification Search
None
See application file for complete search history.

(56) References Cited

U.S. PATENT DOCUMENTS

| | | | | |
|---|---|---|---|---|
| 5,523,204 A * | 6/1996 | Singer | ................ | C12Q 1/6841 435/5 |
| 5,672,696 A | 9/1997 | Wang et al. | | |
| 2004/0091880 A1* | 5/2004 | Wiebusch | ............ | C12Q 1/6841 435/6.11 |
| 2010/0120060 A1 | 5/2010 | Philipsen et al. | | |
| 2010/0216652 A1 | 8/2010 | Eberwine et al. | | |
| 2013/0023433 A1* | 1/2013 | Luo | .................... | C12Q 1/6841 506/9 |
| 2013/0027518 A1 | 1/2013 | MacKay et al. | | |
| 2014/0162378 A1 | 6/2014 | Hanashi | | |
| 2015/0051101 A1* | 2/2015 | Hoshino | ............ | G01N 33/5306 506/9 |

FOREIGN PATENT DOCUMENTS

| | | |
|---|---|---|
| JP | H08-33500 A | 2/1996 |
| JP | H10-123027 A | 5/1998 |

OTHER PUBLICATIONS

Michael Neumann et al., "Simple Method for Reduction of Autofluorescence in Fluorescence Microscopy", The Journal of Histochemistry & Cytochemistry, 2002, pp. 437-439, vol. 50(3), The Histochemical Society, Inc., Bremen, Germany.
M.S. Viegas et al., "An improved and cost-effective methodology for the reduction of autofluorescence in direct immunofluorescence studies on formalin-fixed paraffin-embedded tissues", 2007, pp. 59-66, vol. 51 issue 1(Jan.-Mar.), European Journal of Histochemistry, Coimbra, Portugal.
Karl Kingsley et al., "Photobleaching of Arterial Autofluorescence for Immunofluorescence Applications", BioTechniques, Apr. 2001, vol. 30, No. 4, pp. 794-797, Las Vegas, NV, USA.
Tomas Hirschfeld, "Fluorescence Background Discrimination by Prebleaching", The Journal of Histochemistry and Cytochemistry, 1979, vol. 27, No. 1, pp. 96-101, The Histochemical Society, Inc., Cambridge, Massachusetts, USA.
C. H. Tse et al, "Determining True HER2 Gene Status in Breast Cancers With Polysomy by Using Alternative Chromosome 17 Reference Genes: Implicatins for Anti-HER2 Targeted Therapy", Journal of Clinical Oncology, Sep. 26, 2011 (Sep. 26, 2011), pp. 4168-4174, XP055294464, vol. 29, No. 31, US ISSN: 0732-183X, DOI: 10.1200/JCO.2011.36.0107.
Anonymous, "Photobleaching", Wikipedia, the free encyclopedia, Feb. 24, 2013, 2 pages, Retrieved from the Internet: URL: https://web.archive.org/web/20130224025400/https://en.wikipedia.org/wiki/Photobleaching [Retrieved on Dec. 14, 2017].
Mihovilovic M et al: "An efficient method for sequencing PCR amplified DNA", Biotechniques, Jan. 1, 1989, p. 14-6, vol. 7, No. 1: 14-6 , Retrieved from the Internet: URL: http://www.ncbi.nlm.nih.gov/pubmed/2534272.
Anonymous: "Polymerase chain reaction", Wikipedia, the free encyclopedia, Mar. 24, 2015, Retrieved from the Internet: URL: https://web.archive.org/web/20150324071128/https://en.wikipedia.org/wiki/Polymerase_chain_reaction.
Irvine Scott E. et al., Direct Light-Driven Modulation of Luminescence from Mn-Doped ZnSe Quantum Dots, Angewandte Chemie International Edition, Feb. 27, 2008, p. 2685-2688, vol. 47, No. 14 ;Cited in the communication pursuant to Article 94(3) EPC dated Dec. 10, 2018 in the counterpart European patent application.
Lesoine Michael D. et al., Subdiffraction, Luminescence-Depletion Imaging of Isolated, Giant, CdSe/CdS Nanocrystal Quantum Dots, The Journal of Physical Chemistry C, Feb. 7, 2013, p. 3662-3667, vol. 117, No. 7; Cited in the communication pursuant to Article 94(3) EPC dated Dec. 10, 2018 in the counterpart European patent application.
Anonymous,Confocal microscopy, Retrieved from the Internet, Feb. 23, 2015, URL:https://web.archive.org/web/20150213203150/https://en.wikipedia.org/wiki/Confocal_microscopy; Cited in the communication pursuant to Article 94(3) EPC dated Dec. 10, 2018 in the counterpart European patent application.

(Continued)

*Primary Examiner* — Robert T. Crow
(74) *Attorney, Agent, or Firm* — Metrolex IP Law Group, PLLC

(57) ABSTRACT

A sample analyzing method includes: denaturing DNA by heating a measurement specimen; bleaching the measurement specimen to inhibit autofluorescence from the measurement specimen; binding a fluorescent dye to a test substance in the measurement specimen; and capturing an image of fluorescence originated from the fluorescent dye by irradiating the measurement specimen with light. The DNA denaturation treatment is performed before the bleaching.

7 Claims, 12 Drawing Sheets

(56) References Cited

OTHER PUBLICATIONS

Katsumasa Fujita, Chemical and Bioimaging, Chemistry and living organisms, 2011, vol. 49, No. 12, pp. 852-856, cited in the Japanese Office Action (JPOA) dated Mar. 12, 2019 in a counterpart Japanese patent application.

The Japanese Office Action (JPOA) dated Mar. 12, 2019 in a counterpart Japanese patent application.

Takehiko Koji, "Evidence for heterogeneous distribution of specific RNA molecules in the cytoplasm by light microscopic in situ hybridization", Electron-Microscopy, 2002, pp. 77-80, vol. 37, No. 2, Japanese Society of Microscopy; Cited in the Japanese Office Action (JPOA) dated Nov. 5, 2019 in a counterpart Japanese patent application.

Japanese Office Action (JPOA) dated Nov. 5, 2019 in a counterpart Japanese patent application.

C. H. Tse et al, "Determining True HER2 Gene Status in Breast Cancers With Polysomy by Using Alternative Chromosome 17 Reference Genes: Implications for Anti-HER2 Targeted Therapy", Journal of Clinical Oncology, Sep. 26, 2011 (Sep. 26, 2011), pp. 4168-4174, XP055294464, vol. 29, No. 31, US ISSN: 0732-183X, DOI: 10.1200/JCO.2011.36.0107.

* cited by examiner

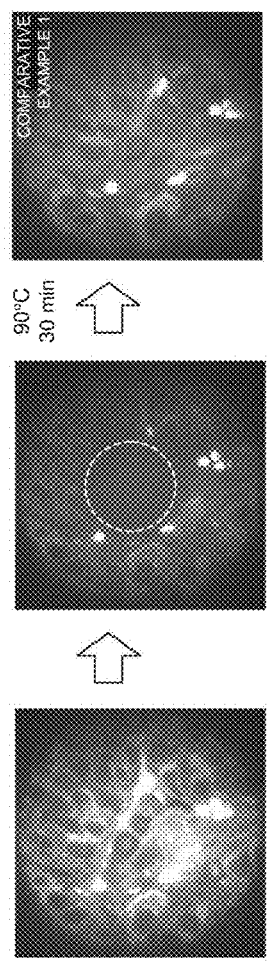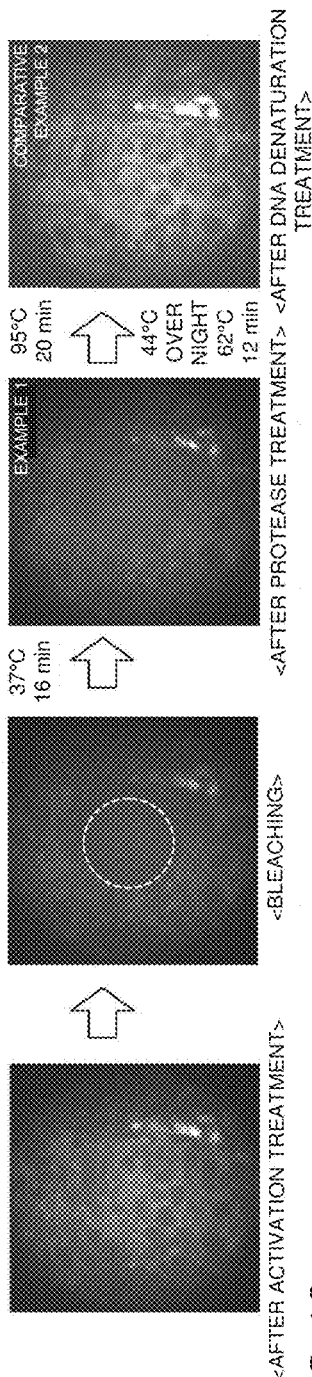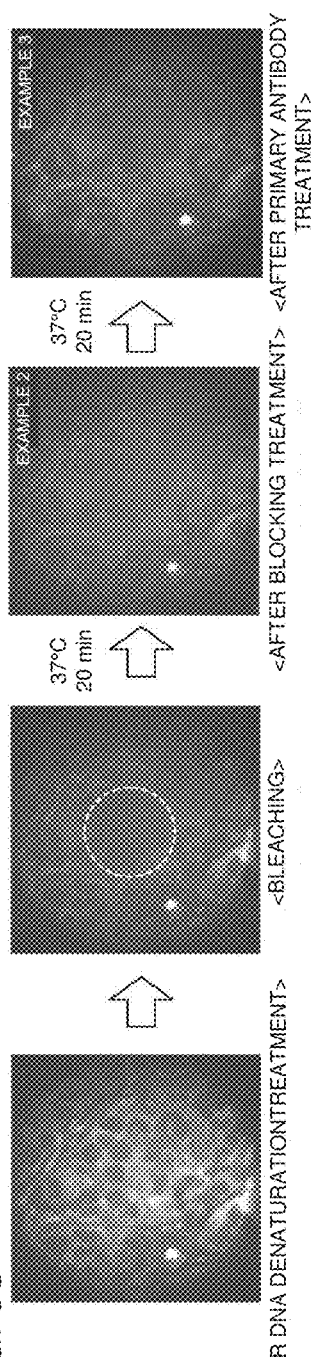
FIG. 6A
FIG. 6B
FIG. 6C

FIG. 7

| treatment process | temperature | example 1 | example 2 | example 3 | comparative example 1 | comparative example 2 |
|---|---|---|---|---|---|---|
| deparaffinization treatment | 65°C | ○ | ○ | ○ | ○ | ○ |
| bleaching | × | × | × | × | ○ | × |
| activation treatment | 90°C | ○ | ○ | ○ | ○ | ○ |
| bleaching | × | ○ | × | × | × | ○ |
| protease treatment | 37°C | ○ | ○ | ○ | × | ○ |
| DNA denaturation treatment | 90 °C (thermal denaturation) 44 °C (hybridization) 62 °C (stringency cleaning) | × | ○ | ○ | × | ○ |
| bleaching | × | × | ○ | ○ | × | × |
| blocking treatment | 37°C | × | ○ | ○ | × | × |
| primary antibody treatment | 37°C | × | × | ○ | × | × |
| level of recovery of autofluorescence | | + | + | + | +++ | ++++ |

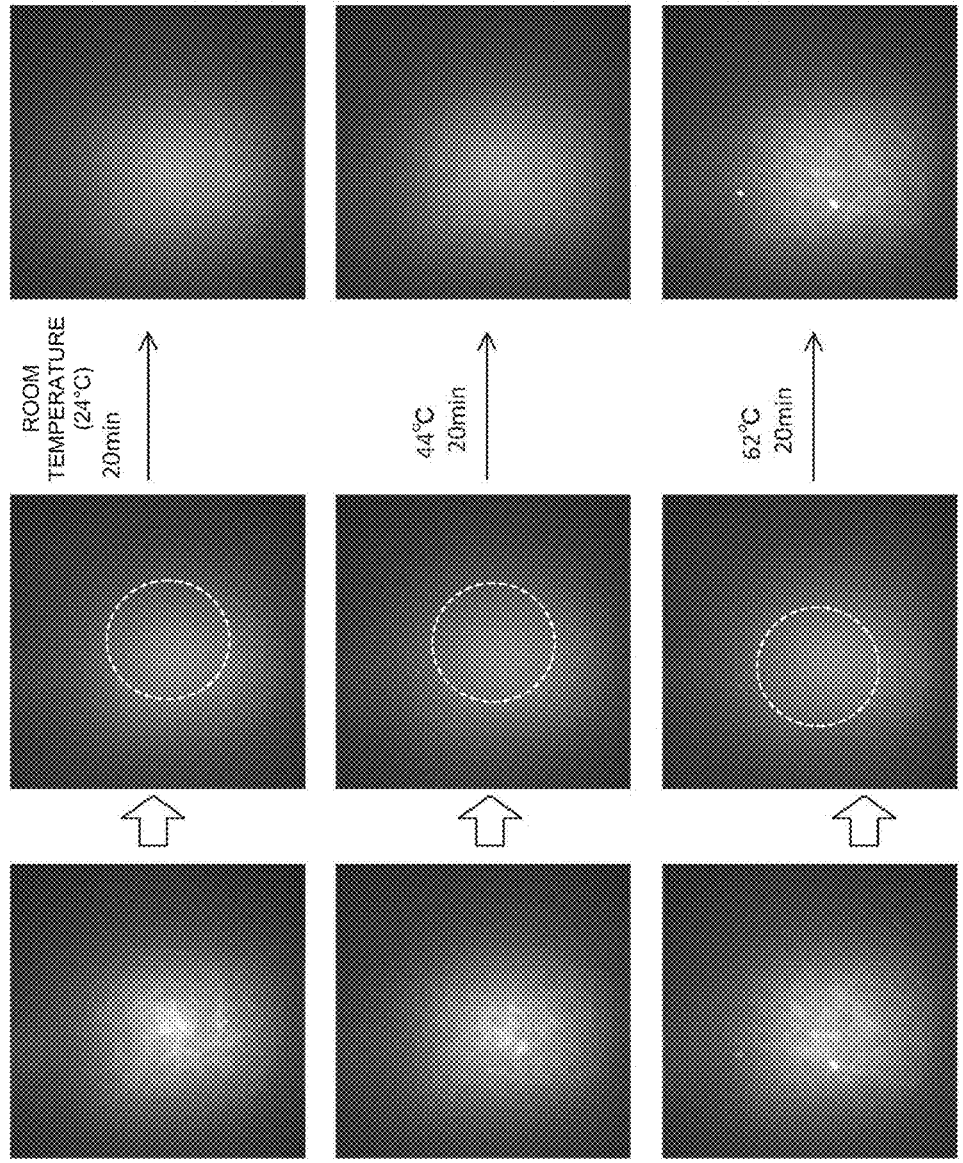

SAMPLE ANALYZING METHOD AND SAMPLE ANALYZER

CROSS REFERENCE TO RELATED APPLICATIONS

This application claims priority based on 35 USC 119 from prior Japanese Patent Application No. 2015-065666 filed on Mar. 27, 2015, entitled "SAMPLE ANALYZING METHOD AND SAMPLE ANALYZER", the entire contents of which are hereby incorporated by reference.

BACKGROUND

The disclosure relates to a sample analyzing method and a sample analyzer of analyzing a test substance in a measurement specimen by use of a captured image obtained by capturing an image of the measurement specimen.

The progress in the condition of some disease is affected by a specific gene, a specific protein, or the like. Checking on the presence and condition of a specific substance in a cell taken from a subject is very useful to diagnose such a disease and determine a treatment policy.

The detection of a specific substance is achieved, for example, by labeling the specific substance with a fluorescent dye, and capturing an image of fluorescence originated from the fluorescent dye. The irradiation of a measurement specimen including a test cell with light excites the fluorescence from the fluorescent dye. In this regard, some measurement specimen may emit autofluorescence when the measurement specimen is irradiated with light for excitation. This autofluorescence works as background noise against the fluorescence originated from the fluorescent dye.

US Patent Application Publication No. US2010/0120060A1 discloses a method of inhibiting this autofluorescence. The method disclosed in US Patent Application Publication US2010/0120060A1 inhibits the emission of the autofluorescence by irradiating the measurement specimen with light. The inhibition of the autofluorescence by giving a predetermined effect to a measurement specimen in this manner is generally referred to as "bleaching".

SUMMARY

A sample analyzing method according to a first embodiment includes: a DNA denaturation treatment process for denaturing DNA by heating a measurement specimen; a bleaching process for inhibiting autofluorescence from the measurement specimen; a labeling process for binding a fluorescent dye to a test substance in the measurement specimen; and an image capture process for capturing an image of fluorescence from the fluorescent dye by irradiating the measurement specimen with light. The sample analyzing method performs the DNA denaturation treatment process before the bleaching process.

A sample analyzer according to a second embodiment includes: a pretreatment section that pretreats a measurement specimen to capture an image of a test substance included in the measurement specimen; an image capture section that captures an image of the measurement specimen which the pretreatment section pretreats; and an analysis section that extracts the test substance by processing the captured image which the image capture section obtains. The pretreatment section includes a first treatment unit that performs a DNA denaturation treatment for denaturing DNA by heating the measurement specimen, a second treatment unit that performs a bleaching treatment for inhibiting autofluorescence from the measurement specimen, and a third treatment unit configured to perform a labeling treatment for binding a fluorescent dye to the test substance in the measurement specimen. The first treatment unit that performs the DNA denaturation treatment treats the measurement specimen before the second treatment unit performs the bleaching treatment. The image capture section captures an image of fluorescence from the fluorescent dye by irradiating the pretreated measurement specimen with light.

BRIEF DESCRIPTION OF DRAWINGS

FIG. 6A illustrates diagrams each representing a result of Examination 1 of the embodiment on autofluorescence in the case of: performing a bleaching treatment immediately after a deparaffinization treatment; and thereafter performing an activation treatment. FIG. 6B illustrates diagrams each representing a result of Examination 1 of the embodiment on the autofluorescence in the case of: performing the bleaching treatment immediately after the activation treatment; and thereafter performing a protease treatment and a DNA denaturation treatment in this order. FIG. 6C illustrates diagrams representing a result of Examination 1 of the embodiment on the autofluorescence in the case of: performing the bleaching treatment immediately after the DNA denaturation treatment; and thereafter performing a blocking treatment and a primary antibody treatment in this order.

FIG. 7 is a table summarizing the results of Examination 1 of the embodiment.

FIG. 8A illustrates captured images obtained by capturing images of recovery of the autofluorescence in Examination 2 of the embodiment in the case of leaving a measurement specimen at room temperature for 20 minutes after performing the bleaching treatment on the measurement specimen. FIG. 8B illustrates captured images obtained by capturing images of recovery of the autofluorescence in Examination 2 of the embodiment in the case of heating a measurement specimen at 44° C. for 20 minutes after performing the bleaching treatment on the measurement specimen. FIG. 8C illustrates captured images obtained by capturing images of recovery of the autofluorescence in Examination 2 of the embodiment in the case of heating a measurement specimen at 62° C. for 20 minutes after performing the bleaching treatment on the measurement specimen.

DETAILED DESCRIPTION

An embodiment shown below is an application of the invention to a sample analyzing method and a sample analyzer of analyzing abreast cancer using a measurement specimen taken from diseased tissue of a subject. In this embodiment, HER2 gene which is a prognostic factor of the breast cancer is detected as a test substance. When an image of the HER2 gene labeled with a fluorescent dye is captured, intrinsic emission of light from the measurement specimen, that is to say, autofluorescence of the measurement specimen, works as background noise, and thus decreases accuracy with which to detect the test substance. The inventors have found a method of effectively inhibiting the autofluorescence, which arises from the measurement specimen, in a pretreatment process of pretreatment the measurement specimen. Descriptions are hereinbelow provided for the method together with the inventors' examinations.

1. Basic Process

Figure 1:
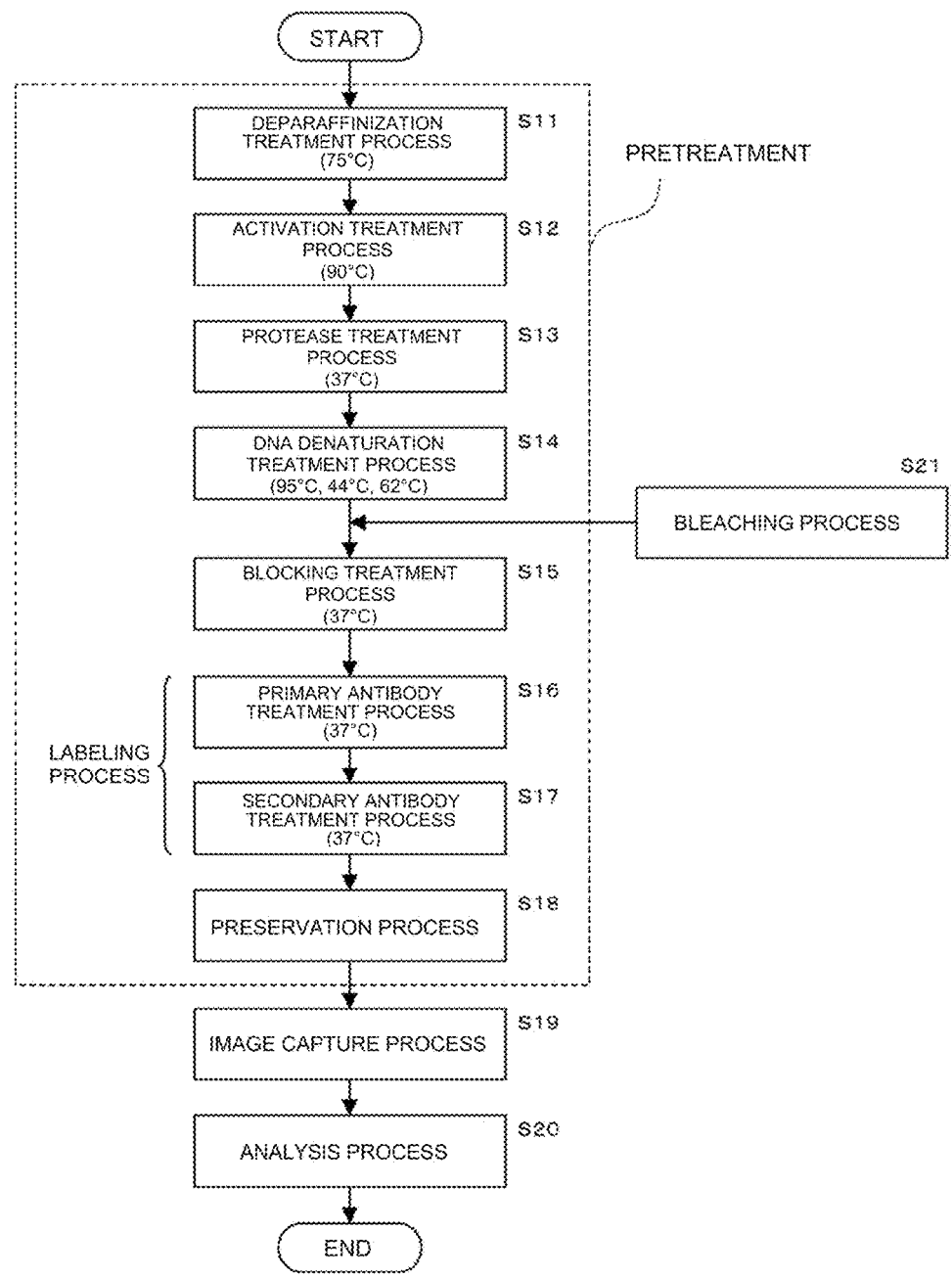
FIG. 1 is a flow chart illustrating treatments included in a sample analyzing method of an embodiment.

As illustrated in FIG. 1, the sample analyzing method performs a deparaffinization treatment process, an activation treatment process, a protease treatment process, a DNA denaturation treatment process, a blocking treatment process, a primary antibody treatment process, a secondary antibody treatment process and a preservation process, as the pretreatment process for the measurement specimen taken from the diseased tissue of the subject. Concrete treatment contents, inclusive of reagents used in the treatment processes, are shown in the examinations described below. Here, comprehensive descriptions are provided for what treatment is performed in each treatment process.

The deparaffinization treatment process in step S11 is a treatment process of removing paraffin from the measurement specimen. The paraffin is used on the measurement specimen in order to preserve a tissue section as the measurement specimen. In step S11, the paraffin is removed from the measurement specimen in order to make a stained probe, that is, DNP-labeled nucleic acid or a dye-labeled antibody, easily enter a cell in the measurement specimen. In step S11, the treatment is performed by raising the temperature of the measurement specimen to 75° C. The treatment may be performed at a temperature not less than 44° C., at which paraffin melts, but not greater than 100° C.

The activation treatment process in step S12 and the protease treatment process in step S13 are treatment processes of enhancing reactivity of the nucleic acid in the cell. In steps S12 and S13, methylene bridges and the like are broken and antigens are activated; and peptide bonds of specific amino acid residues are broken. In step S12, the treatment is performed by raising the temperature of the measurement specimen to 90° C. In step S13, the treatment is performed by raising the temperature of the measurement specimen to 37° C.

The DNA denaturation treatment process in step S14 includes a DNA denaturation treatment, a hybridization treatment and a stringency cleaning treatment. Through the treatments in step S14, the double-stranded DNA is separated into two independent single-stranded DNA. Thereby, part of the DNA to which the stained probe, or the DNP-labeled nucleic acid, is bound is exposed. The two thus-separated strands of the DNA are inhibited from being bound together again by keeping the DNA at a high temperature of 95° C. Thereafter, by lowering the temperature to 44° C., the DNP-labeled nucleic acid probe is bound to the binding part of the DNA. The temperature appropriate for this reaction varies depending on the nucleic acid probe sequence and the solution composition inclusive of salt concentration. The temperature for the reaction is within a range not less than room temperature but not greater than 80° C. After that, the stringency cleaning is performed at 62° C. The temperature for the stringency cleaning is higher than temperature at which the nucleic acid probe is bound to the binding part of the DNA. In step S14, the treatments are performed by raising the temperature to 95° C., 44° C. and 62° C., respectively.

The blocking treatment process in step S15 is a treatment process of applying a blocking treatment to the tissue section in order to prevent antibodies for labeling the nucleic acid probe with fluorescence, that is to say, a primary antibody and a secondary antibody, from being nonspecifically bound to the tissue section of the measurement specimen. This treatment reduces noise on captured images. In step S15, the treatment is performed by raising the temperature of the measurement specimen to 37° C. in order to shorten the reaction time. No problem arises even if the reaction in step S15 is performed at room temperature, that is to say, at approximately 24° C.

The primary antibody treatment process in step S16 is a treatment process of binding the primary antibody to the DNP-labeled nucleic acid probe bound to the test substance in the measurement specimen. The secondary antibody treatment process in step S17 is a treatment process of further binding the fluorescent dye, or the fluorescence-labeled secondary antibody, to the primary antibody bound to the DNP-labeled nucleic acid probe. Steps S16 and S17 are labeling steps of labeling the test substance in the measurement specimen with fluorescence. In steps S16 and S17, the respective treatments are performed by raising the temperature of the measurement specimen to 37° C. in order to shorten the respective reactions times. No problem arises even if the reactions in step S16 and S17 are performed at room temperature, that is to say, at approximately 24° C.

In a case where in addition to the HER2 gene, a different substance such as CEP17 is a test substance, a labeling treatment is performed on the different test substance in steps S14, S16 and S17 as well. In the secondary antibody treatment process in step S17, a nucleus in the measurement specimen may be simultaneously stained using a nucleus-staining dye.

Figure 2:
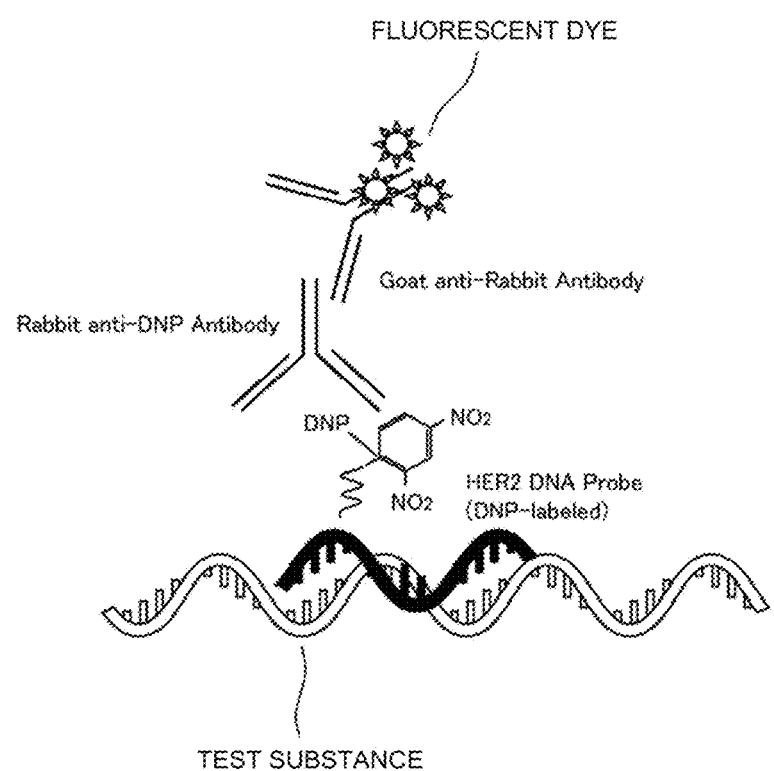
FIG. 2 is a diagram illustrating how a fluorescent dye of the embodiment is bound to a test substance.

As illustrated in FIG. 2, the primary antibody is bound to the DNP-labeled nucleic acid probe bound to the HER2 gene as the test substance, and the secondary antibody is bound to the thus-bound primary antibody. The secondary antibody includes the fluorescent dye. The fluorescent dye included in the secondary antibody may be switchable between an activated state in which the fluorescent dye emits fluorescence when irradiated with light for fluorescence excitation and an inactivated state in which the fluorescent dye emits no fluorescence even when irradiated with the light for fluorescence excitation. In the embodiment, if while in the activated state, the fluorescent dye with which the HER2 gene is labeled is irradiated with the light for fluorescence excitation with a predetermined intensity for a predetermined length of time, emits fluorescence and enters the inactivated state. Thereafter, when irradiated with light whose wavelength is different from that of the light for fluorescence excitation, the fluorescent dye is activated. Hereinafter, the inactivation is referred to as "fluorescence quenching." The fluorescent dye may be activated by an act of heat, a chemical agent or the like on the fluorescent dye instead of the act of the light on the fluorescent dye.

Returning to FIG. 1, the preservation process in step S18 is a process of: cleaning and drying the measurement specimen treated in steps in S11 to S17; and preserving the resultant measurement specimen in the dark until images of the measurement specimen are captured. In a case where images of the measurement specimen are captured immediately after it is cleaned and dried, it does not have to be preserved in the dark.

An image capture process in step S19 is a process of capturing images of the pretreated measurement specimen. In step S19, images of the fluorescence emitted from the fluorescent dye bound to the test substance are captured. An analyzing process in step S20 is a process of: analyzing the captured images obtained in the image capture process in step S19; and detecting and counting the number of test substances included in the cell.

Figure 3:
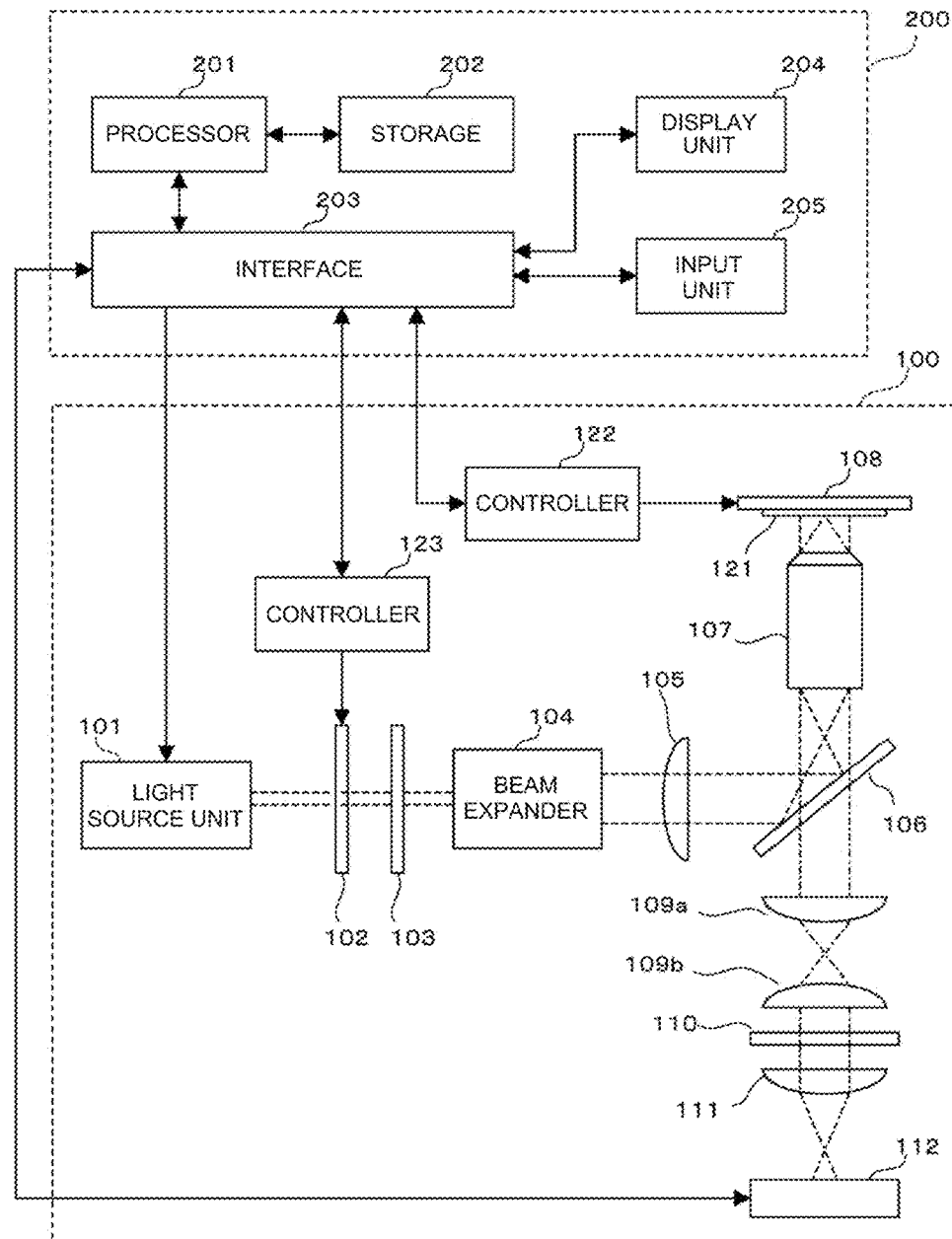
FIG. 3 is a diagram illustrating configuration of an image capture section and an analysis section of the embodiment.

The image capture process in step S19 is performed using image capture section 100 illustrated in FIG. 3, for example. The analyzing process in step S20 is performed using analysis section 200 illustrated in FIG. 3, for example. Under control of processor 201 of analysis section 200, image capture section 100 performs an image capture process on the measurement specimen.

Image capture section 100 includes light source unit 101, shutter 102, ¼ wavelength plate 103, beam expander 104, collective lens 105, dichroic mirror 106, objective lens 107, stage 108, beam expander 109, phase plate 110, collective lens 111, and picture device 112. Picture device 112 is, for example, a CCD, an EMCCD, a CMOS, or a scientific CMOS image sensor. Slide glass 121 on which the measurement specimen is placed is set on stage 108.

Light source unit 101 emits two beams of light whose wavelengths are different from each other. A beam of light with a first wavelength excites fluorescence of the fluorescent dye bound to the HER2 gene as the test substance. A beam of light with a second wavelength excites fluorescence of the dye with which the nucleus is stained. The beam of light with the second wavelength is used to activate the fluorescent dye bound to the HER2 gene as well. The first wavelength is 640 nm, for example. The second wavelength is 405 nm, for example. In the case where in addition to the HER2 gene, CEP17 or the like is used as another test substance, light source unit 101 further emits a beam of light with a third wavelength. The third wavelength is 750 nm, for example. Light source unit 101 includes, for example, light sources configured to emit the beams of light with the respective wavelengths, and a dichroic mirror configured to make the optical axes of the beams of light coincide with one another. It is desirable that a laser light source be used for light source unit 101. However, a mercury lamp, a Xenon lamp, an LED or the like may be used for light source unit 101.

Shutter 102 is driven by controller 123. Controller 123 switches shutter 102 between a condition in which shutter 102 allows any beam of light emitted from light source unit 101 to pass through shutter 102 and a condition in which shutter 102 blocks the beam of light emitted from light source unit 101. Thereby, shutter 102 adjusts a length of time for which to irradiate the test substance with the beam of light.

¼ wavelength plate 103 converts the linearly-polarized beam of light emitted from light source unit 101 into a circularly-polarized beam of light, respectively. The fluorescent dye reacts to the beam of light in a predetermined polarization direction. For this reason, the conversion of the beam of light for fluorescence excitation into the circularly-polarized beam of light makes it easy for the polarization direction of the beam of light for fluorescence excitation to coincide with the polarization direction in which the fluorescent dye reacts. This makes it possible to efficiently excite the fluorescence of the fluorescent dye included in the test substance. In a case where the beam of light for fluorescence excitation are not converted into the circularly-polarized beam of light, that is to say, in a case where the excitation efficiency is not taken into consideration, ¼ wavelength plate 103 may be omitted. Beam expander 104 expands a light irradiation area on slide glass 121. Collective lens 105 collects the beam of light in order that parallel beams are made incident onto slide glass 121 from objective lens 107.

Dichroic mirror 106 reflects the beam of light emitted from light source unit 101, and transmits the fluorescence emitted from the test substance. Objective lens 107 guides the beam of light reflected off dichroic mirror 106 to slide glass 121. Stage 108 is driven by controller 122, and moves in a horizontal plane. Thereby, the beam of light is incident onto a wide area on slide glass 121. The fluorescence emitted from the test substance passes through objective lens 107, and dichroic mirror 106 transmits the resultant fluorescence.

Lens 109a collects the fluorescence which passes through dichroic mirror 106, and forms an image of the fluorescence. Phase plate 110 is disposed on the Fourier plane formed by lens 109b. Phase plate 110 exerts a phase modulation effect on the fluorescence which passes through beam expander 109. Collective lens 111 collects the fluorescence which passes through phase plate 110, and guides the resultant fluorescence to a light reception surface of picture device 112. Picture device 112 captures an image of the fluorescence, and outputs the captured image to analysis section 200.

Figure 4A:
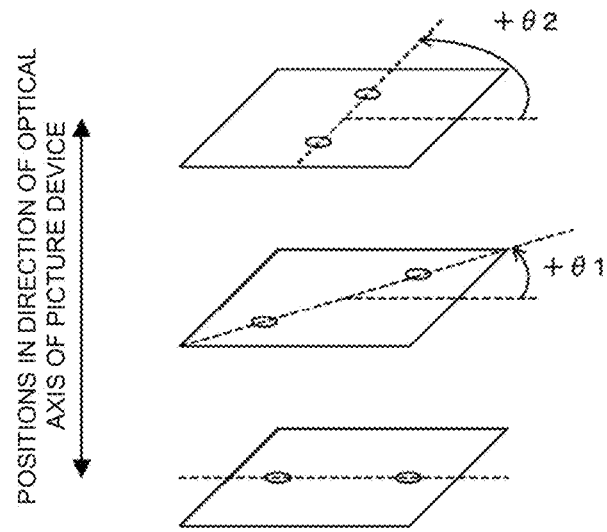
FIG. 4A is a diagram illustrating how two focal points of the embodiment rotate on a light reception surface in accordance with a position of a luminescent point of fluorescence in a direction of an optical axis.

Phase plate 110 is disposed on the Fourier plane, and exerts a point spread function modulating effect in a way that two focal points appear on the light reception surface of picture device 112. Through the effect exerted by phase plate 110, the fluorescence emitted from one fluorescent dye in the measurement specimen forms two images respectively at the two focal points on the light reception surface of picture device 112. In this event, as illustrated in FIG. 4A, the two focal points turns on the light reception surface in accordance with a position of the luminescent point of the fluorescence in a direction of the optical axis of objective lens 107. In other words, an angle of the straight line joining the two focal points to the straight line representing the reference changes on the light reception surface of picture device 112 in accordance with the position of the luminescent point of the fluorescence in the direction of the optical axis.

For example, if there are two fluorescent dyes respectively at two positions on slide glass 121 which are different from each other in the direction of the optical axis of objective lens 107, phase plate 110 divides the fluorescence emitted from each fluorescent dye into two beams of fluorescence, which fall incident onto the light reception surface of picture device 112. In this case, for example, with regard to one of the two fluorescent dyes, the angle of the straight line joining the two focal points to the straight line representing the reference is at +θ1; and with regard to the other fluorescent dye, the angle of the straight line joining the two focal points to the straight line representing the reference is at +θ2, as illustrated in FIG. 4A. Accordingly, for each fluorescent dye, it is possible to obtain the position of the fluorescent dye in the direction of the optical axis by obtaining the angle of the straight line joining the two focal points to the straight line representing the reference.

Returning to FIG. 3, analysis section 200 is a personal computer, for example. Analysis section 200 includes processor 201, storage 202, interface 203, display unit 204 and input unit 205.

Processor 201 is a CPU, for example. Storage 202 includes a ROM, a RAM and a hard disk. Processor 201 executes various functions based on programs stored in storage 202. Processor 201 processes an image obtained by picture device 112, and performs a variety of other processes. Furthermore, processor 201 controls light source unit 101, picture device 112, and controllers 122, 123 via interface 203. Display unit 204 is a display on which to display results of the processes performed by processor 201, and the like. Input unit 205 includes a keyboard and a mouse for receiving input of instructions from the user.

In the image capture process in step S19 in FIG. 1, processor 201 of analysis section 200 obtains images of the nucleus in the measurement specimen and images of the fluorescent dyes bound to the test substance by controlling light source unit 101 and picture device 112. In the analyzing process in step S20 in FIG. 1, processor 201 detects the nucleus and the fluorescent dyes from the images obtained in step S19. Based on the images of the nucleus and the images of the florescent dyes, processor 201 counts the number of test substances, that is to say, the number of HER2 genes.

Figure 4B:
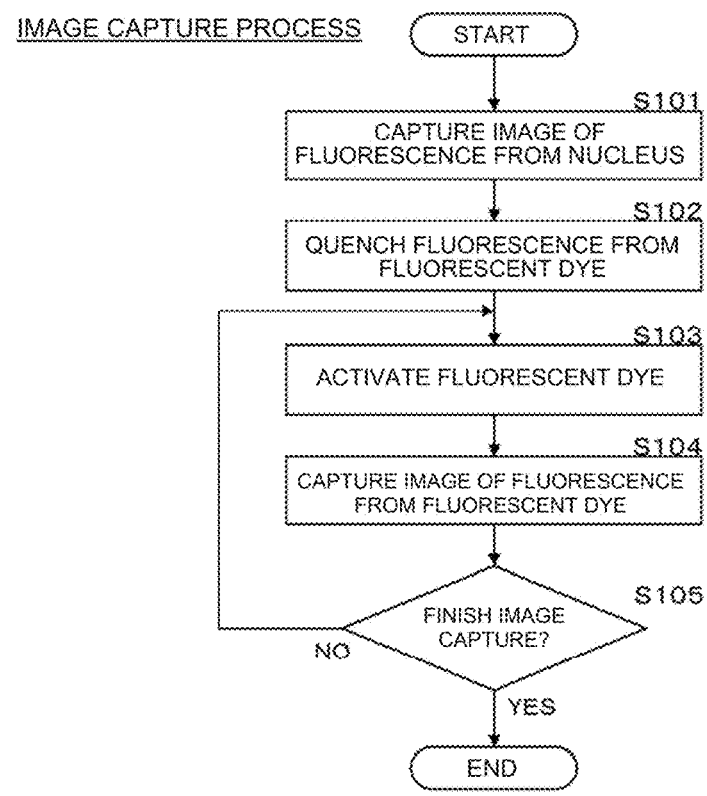
FIG. 4B is a flowchart illustrating processes performed in an image capture process of the embodiment.

As illustrated in FIG. 4B, in step S101, processor 201 irradiates the measurement specimen with the beam of light with the second wavelength from light source unit 101, and thereby makes the dye with which the nucleus is stained emit the fluorescence. Processor 201 captures images of the thus-emitted fluorescence using picture device 112, and thereby obtains the images of the nucleus. Processor 201 obtains a predetermined number of images of the nucleus, for example 100 images of the nucleus, by repeating the image capturing while irradiating the measurement specimen with the beam of light. The number of images captured in step S101 is not limited to 100, and may be one, for example. For each of the focus positions which are different from each other in the direction of the optical axis, processor 201 performs the above-described image obtaining process on the nucleus by displacing objective lens 107 in the direction of the optical axis. Thereby, processor 201 obtains 100 images of the nucleus from each focus position.

In step S102, processor 201 irradiates the measurement specimen with the beam of light with the first wavelength from light source unit 101, and thereby quenches fluorescence of the fluorescent dyes bound to the test substance. In step S103, processor 201 irradiates the measurement specimen with the beam of light with the second wavelength from light source unit 101, and thereby activates the fluorescent dyes bound to the test substance. In step S104, processor 201 irradiates the measurement specimen with the beam of light with the first wavelength from light source unit 101, and thereby makes the fluorescent dyes emit the fluorescence. Processor 201 captures the thus-emitted fluorescence using picture device 112.

In step S104, processor 201 obtains a predetermined number of images of the fluorescence, for example 100 images of the fluorescence, by repeating the image capturing while irradiating the measurement specimen with the beam of light with the first wavelength. The number of images captured in step S104 is not limited to 100, and may be one, for example. In step S104, while processor 201 is irradiating the measurement specimen with the beam of light with the first wavelength from light source unit 101, the beam of light with the first wavelength quenches the fluorescence of the fluorescent dyes bound to the test substance.

In step S105, processor 201 judges whether or not processor 201 finishes capturing images of the fluorescence. Processor 201 repeats the processes in steps S103, S104 a predetermined number of times. For example, processor 201 repeats the processes in steps S103, S104 30 times. For this reason, processor 201 obtains 3000 captured images of the fluorescence. As illustrated in FIG. 4(a), the fluorescence emitted from each fluorescent dye forms its images respectively at the two focal points on the light reception surface of picture device 112. As a result, each captured image of the fluorescence includes as many pairs of luminescent spots as fluorescent dyes activated in step S103.

In step S103, not all of the fluorescent dyes bound to the test substance are activated. A large number of fluorescent dyes are bound to one test substance. In step S103, a predetermined percentage of the fluorescent dyes bound to one test substance are activated. The same fluorescent dyes are not always activated every time the activation process in step S103 is repeatedly performed. The distribution of fluorescent dyes activated by each activation process is at random.

Processor 201 repeats the activation process, the image capture process and the inactivation process the multiple times through the processes insteps S103, S104. Thereby, processor 201 is capable of dispersing the fluorescence from the fluorescent dyes in each captured image while making the fluorescent dyes emit the fluorescence without exception. Thereby, processor 201 is capable of smoothly extracting the luminescent spots based on the fluorescent dyes from each captured image.

Figure 5A:
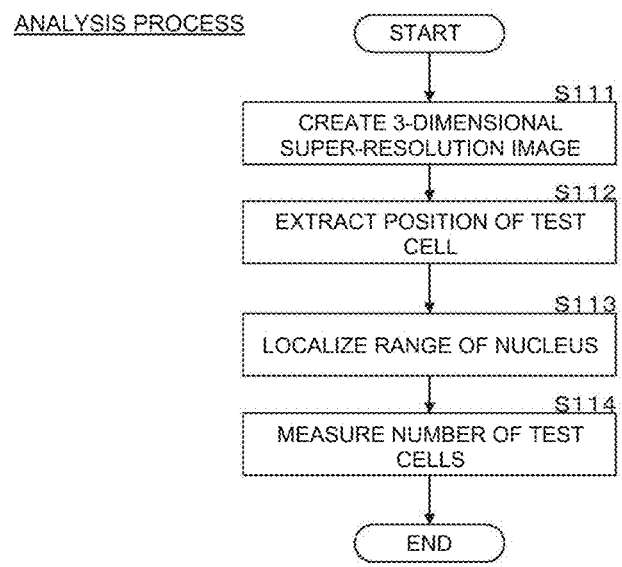
FIG. 5A is a flowchart illustrating treatments performed in an analysis process of the embodiment.

As illustrated in FIG. 5A, in step S111, processor 201 obtains a three-dimensional super-resolution image from the captured images of the fluorescent dyes obtained by repeating the fluorescence quenching and the activation as described above. The three-dimensional super-resolution image is an image showing the distribution of test substances in the three-dimensional space. In step S111, processor 201 extracts luminescent spots of the fluorescence by performing Gauss fitting on the captured images of the fluorescent dyes, and further obtains the luminescence brightnesses of the extracted luminescent spots. Subsequently, processor 201 pairs each two luminescent spots whose luminescence brightnesses are almost equal to each other, and the distance between which is within a predetermined range. Thereafter, processor 201 fits the paired two luminescent spots to a template for two luminescent spots which is stored in storage 202 in advance. Processor 201 judges that the paired two luminescent spots which can be fitted together with certain accuracy or higher accuracy are based on the division of the fluorescence from one fluorescent dye by phase plate 110.

Figure 5B:
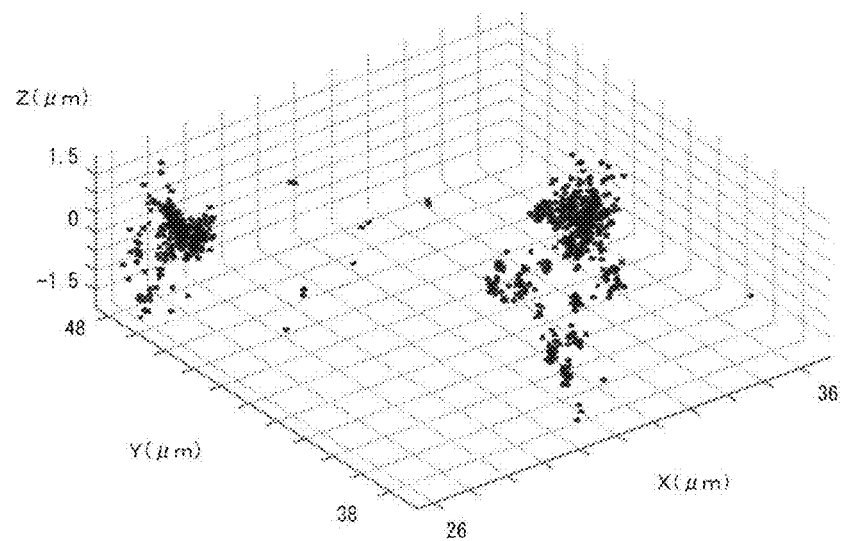
FIG. 5B is a diagram illustrating a three-dimensional super-resolution image of the embodiment.

After that, processor 201 judges that the middle point between the paired two luminescent spots on the light reception surface is the position of the fluorescent dye in the two-dimensional plane in the image capture field. As describe above, based on the angle of the straight line joining the paired two luminescent spots to the straight line representing the reference, processor 201 determines the position of the fluorescent dye in the direction of the optical axis of objective lens 107. In this manner, processor 201 identifies the coordinate point of each of the fluorescent dyes relative to the three-dimensional coordinate axes on the basis of the position of the fluorescent dye in the two-dimensional plane and the position of the fluorescent dye in the direction of the optical axis. Processor 201 creates the three-dimensional super-resolution image by superposing the thus-identified coordinate points in all the captured images. Thereby, processor 201 obtains the three-dimensional super-resolution image illustrated in FIG. 5B, for example. In FIG. 5B, the X-Y plane represents the two-dimensional plane in the image capture field, while the Z-axis direction represents the direction of the optical axis of objective lens 107.

In step S112, processor 201 extracts test substances by classifying the identified coordinate points into groups corresponding to the test substances. Processor 201 performs the grouping on the coordinate points, for example, as follows. Processor 201 scans predetermined reference spaces in the three-dimensional coordinate system; extracts the position of a reference space in which the number of coordinate points included therein is greater than a threshold value, and which includes more coordinate points than the vicinity of the reference space; and associates a group of coordinate points included in the reference space at the extracted position with a group corresponding to one test substance. From the thus-classified groups of coordinate points, processor 201 extracts the positions of test substances in the three-dimensional coordinate system.

In step S113, processor 201 obtains a range of the nucleus of the test substance in the three-dimensional space. In step S101 illustrated in FIG. 4B, processor 201 already obtains the captured images of the nucleus at each of the focus positions which are different from each other in the direction of the optical axis. For each focus position, processor 201 averages the images of the nucleus which are obtained at the focus position, and thereby obtains an averaged image of the nucleus at the focus position. For each of the averaged images obtained at the respective focus positions, processor 201 obtains the outline of the nucleus from the area where the fluorescence is obtained. Based on the focus positions and the outlines of the nucleus at the respective focus positions, processor 201 obtains the range of the nucleus in the three-dimensional space.

In step S114, based on the positions of the test substances localized in step S112 and the range of the nucleus obtained in step S113, processor 201 obtains the number of test substances included in the range of the nucleus. With this, processor 201 ends the processes in the analyzing process. Doctors and the like use the number of test substances, or the number of HER2 genes, obtained in step S114 as a benchmark for determining a treatment policy when making a diagnosis. Based on the number of HER2 genes used for the reference, the doctors and the like can grasp the amplitude of the HER2 genes, and can determine the treatment policy including dose administration.

It should be noted that in the case where in addition to the HER2 gene, a different substance such as CEP17 is a test substance, processor 201 obtains captured images of fluorescence emitted from the different test substance, and obtains the number of different test substances included in the nucleus based on the obtained captured images. In the case where the different test substance is CEP17, processor 201 calculates a ratio of the number of HER2 genes included in the nucleus to the number of CEP17 signals included in the nucleus. The doctors and the like use the calculated ratio as a benchmark for determining a treatment policy when making a diagnosis.

Returning to FIG. 1, in steps S19 and S20, processor 201 captures the images of the measurement specimen, and analyzes the test substance based on the captured images as described above. In step S19, it is required that the images of the fluorescence from the nucleus and the images of the fluorescence from the fluorescent dyes bound to the test substance be securely captured. However, the autofluorescence arising from the measurement specimen works as background noise against the fluorescence from the nucleus and the fluorescence from the fluorescent dyes at the image capturing. Particularly because the fluorescence emitted from an individual fluorescent dye is weak, there is likelihood that the fluorescence emitted from the individual fluorescent dye is mixed with the autofluorescence, and cannot be distinguished from the autofluorescence. Furthermore, when as described above, phase plate 110 divides the fluorescence emitted from one fluorescent dye into two beams of fluorescence, the intensity of each of the two beams of fluorescence is weaker. For this reason, the occurrence of the autofluorescence makes it more difficult to distinguish the two beams of fluorescence from the autofluorescence.

It should be noted that although image capture section 100 illustrated in FIG. 3 is configured to divide the fluorescence using phase plate 110, image capture section 100 may include no phase plate 110 to be configured to guide the fluorescence emitted from an individual fluorescent dye to picture device 112 without dividing the fluorescence. In other words, picture device 112 is placed in the image formation plane formed behind lens 109a. In this case, although the position of the individual fluorescent dye cannot be divided in the direction of the optical axis of objective lens 107, it is possible to localize the position of the fluorescent dye in the two-dimensional plane in the image capture field. The intensity of the fluorescence received by picture device 112 is higher when image capture section 100 is thus configured than when as described above, image capture section 100 is configured to divide the fluorescence using phase plate 110. In this case, however, the fluorescence from the individual fluorescent dye is still weak. For this reason, there is likelihood that the autofluorescence arising from the measurement specimen is an obstacle to detecting the fluorescence emitted from the fluorescent dye.

With the foregoing problem taken into consideration, the processing illustrated in FIG. 1 includes a bleaching process in step S21 in order to inhibit the autofluorescence arising from the measurement specimen. In the bleaching process, processor 201 irradiates the measurement specimen with a beam of light with a predetermined wavelength for a predetermined length of time, and thereby inhibits the autofluorescence.

The inventors of this application try to apply a bleaching process to the measurement specimen in the pretreatment process in order to inhibit the autofluorescence arising from the measurement specimen. However, despite performing the bleaching treatment, the inventors cannot inhibit the autofluorescence of the measurement specimen when capturing images of the fluorescence of the fluorescent dye in the image capture process in step S19. As a result, the inventors cannot securely capture the images of the fluorescence arising from the fluorescent dye.

The inventors of this application try hard to find a reason for the failure in inhibiting the autofluorescence through various examinations. Eventually, the inventors find which timing in the pretreatment process is suitable to perform the bleaching process in order to effectively inhibit the autofluorescence of the measurement specimen when capturing images. FIG. 1 illustrates an example of timing for performing the bleaching process in step S21, which is found by the inventors of this application. The bleaching process in step S21 is performed after steps S11, S12, S14 in which the temperature of the measurement specimen is raised to 62° C. or higher. The DNA denaturation treatment process in step S14 is performed before the bleaching process in step S21. The deparaffinization treatment process in step S11 and the activation treatment process in step S12 are also performed before the bleaching process in step S21. Furthermore, no treatment process in which the temperature of the measurement specimen is raised to 62° C. or higher is included between the bleaching process in step S21 and the image capture process in step S19.

The inventors of this application find that the fluorescence from the measurement specimen inhibited in the bleaching process does not recover from the inhibition until the image capture process when using a method of: performing the bleaching process after the treatment processes of applying the respective treatments to the measurement specimen by raising the temperature of the measurement specimen to 62° C. or higher; and performing no treatment process of applying a treatment to the measurement specimen by raising the temperature of the measurement specimen to 62° C. or higher between the bleaching process and the image capture process. The inventors of this application prove that this method enables the fluorescence arising from fluorescent dyes to be securely detected without being affected by the autofluorescence from the measurement specimen.

2. Examinations

The method found by the inventors of this application is hereinbelow explained together with examinations. In the examinations, the inventors of this application label HER2 gene and CEP17 in the pretreatment process. A wavelength for exciting a fluorescent dye used to label the HER2 gene is 640 nm, while a wavelength for exciting a fluorescent dye used to label the CEP17 is 730 nm. A wavelength for exciting a stain used to stain a nucleus is 405 nm. A beam of light with the wavelength of 640 nm quenches the fluorescence of the fluorescent dye used to label the HER2 gene, while a beam of light with the wavelength of 405 nm activates the fluorescent dye. The following examinations are performed to examine the influence of the autofluorescence arising from the nucleus on the fluorescent dye, and the like.

<Pretreatment Process>

In the examinations, the inventors of this application perform the pretreatment process using the following method.

[Measurement Specimen]

Using a Ventana Inform Dual ISH HER2 Kit (Roche Diagnostics K.K.), the inventors stain a human breast cancer cell MCF7 on a HER2 Dual ISH 3-in-1 control slide (ventana) for the purpose of a fluorescence in situ hybridization (FISH) test.

[Deparaffinization Treatment Process]

The inventors dry the control slide on a Dry Block Bath THB (ASONE Corporation) at 65° C. for 20 minutes. The inventors perform deparaffinization by placing EZ Prep on the slide at 75° C. for 7 minutes. After repeating this manipulation five times, the inventors dip the control slide in Reaction Buffer.

[Activation Treatment Process]

The inventors raise the temperature of the Dry Block Bath THB to 90° C., and drops CC2 onto the control slide. Thereafter, the inventors perform conditioning on the control slide for 10 minutes. The inventers add CC2 whenever deemed necessary, in order that the control slide does not become dry. After repeating this manipulation three times, the inventors dip the control slide in Reaction Buffer for four minutes.

[Protease Treatment Process]

The inventors drop ISH Protease II onto the control slide, and cover the control slide with a cover glass. Thereafter, the inventors place the control slide inside a moist chamber placed in an incubator whose temperature is kept at 37° C., and perform an enzymatic treatment on the control slide therein for 16 minutes. Subsequently, the inventors clean the control slide by dipping the control slide in 2×SSC for 4 minutes three times.

[DNA Denaturation Treatment Process]

The inventors drop a liquid mixture obtained by mixing HybReady and HER2 DNA cocktail probes onto the control slide. Thereafter, the inventors cover the control slide with a cover glass, and seal it with paper bond. Subsequently, the inventors place the control slide on the Dry Block Bath THB, and thermally denature the breast cancer cell on the control slide thereon at 95° C. for 20 minutes. After that, the inventors place the control slide inside the moist chamber placed in the incubator whose temperature is kept at 44° C., and perform hybridization on the control slide therein over a night. Afterward, the inventors perform stringency cleaning on the control slide by dipping the control slide in 2×SSC, whose temperature is kept at 62° C., for 4 minutes. After repeating this manipulation three times, the inventors dip the control slide in Reaction Buffer.

[Blocking Treatment Process]

The inventors drop BSA/Reaction buffer with a one-percent concentration onto the control slide, and cover the control slide with a cover glass. Thereafter, the inventors place the control slide inside the moist chamber placed in the incubator whose temperature is kept at 37° C., and perform a blocking treatment on the control slide therein for 20 minutes. Subsequently, the inventors clean the control slide by dipping the control slide in Reaction Buffer.

[Primary Antibody Treatment Process]

The inventors drop a liquid mixture obtained by mixing Rabbit Anti DNA Ab and Mouse Anti DIG Ab onto the control slide, and cover the control slide with a cover glass. Thereafter, the inventors place the control slide inside the moist chamber placed in the incubator whose temperature is kept at 37° C., and make the liquid mixture react on the control slide for 20 minutes. Thereafter, the inventors clean the control slide by dipping the control slide in Reaction Buffer for three minutes. The inventors repeat this manipulation three times.

[Secondary Antibody Treatment Process]

The inventors drop onto the control slide a liquid mixture obtained by diluting Alexa Fluor® 647F(ab')2 fragment of goat anti-rabbit IgG (H+L) (Life Technologies, A-21246), Alexa Fluor® 750 Goat Anti Mouse IgG (H+L) (Life Technologies, A-21037) and Hoechst 33342 (Life Technologies, H1399 diluted in PBS and preserved) with BSA/Reaction buffer with a one-percent concentration, and covers the control slide with a cover glass. Thereafter, the inventors place the control slide inside the moist chamber placed in the incubator whose temperature is kept at 37° C., and make the liquid mixture react on the control slide therein for 20 minutes. Subsequently, the inventors clean the control slide by dipping the control slide in TBST for five minutes. The inventors repeat this manipulation three times.

Alexa Fluor® 647 brand fluorescent dye is a fluorescent dye used to label HER2 gene. Alexa Fluor® 750 brand fluorescent dye is a fluorescent dye used to label CEP 17. Hoechst 33342 is a fluorescent dye used to stain a nucleus.

Alexa Fluor 647 is a fluorescent dye used to label HER2 gene. Alexa Fluor 750 is a fluorescent dye used to label CEP 17. Hoechst 33342 is a fluorescent dye used to stain a nucleus.

[Preservation Process]

The inventors clean the control slide by dipping the control slide in purified water. After repeating this manipulation twice, the inventors dry the control slide inside the incubator, whose temperature is kept at 37° C., for 15 minutes. Thereafter, the inventors preserve the control slide in the dark at 4° C. until an observation.

<Examination 1>

In Examination 1, the inventors check how much the autofluorescence is inhibited by changing timing at which to perform the bleaching process in the pretreatment including the foregoing treatments. Examination 1 proves the effect of inhibiting the autofluorescence in Examples 1 to 3, but shows the autofluorescence is once inhibited and thereafter recovers from the inhibition in Comparative Examples 1 and 2. For each of Examples 1 to 3 as well as Comparative Examples 1 and 2, the inventors perform the bleaching process as follows.

EXAMPLE 1

Before the protease treatment process, the inventors drop Reaction Buffer onto the control slide, and seal the control slide with a cover glass. Thereafter, the inventors set the control slide in a fluorescence microscope, and capture images of the fluorescence. Subsequently, the inventors perform the bleaching treatment on the control slide by irradiating the control slide with a laser beam with a wavelength of 640 nm at a power density of 470 W/cm$^2$ for two minutes. After the protease treatment, the inventors capture images of the fluorescence on the same field of view again.

EXAMPLE 2

Before the blocking treatment process, the inventors drop Reaction Buffer onto the control slide, and seal the control slide with a cover glass. Thereafter, the inventors set the control slide in the fluorescence microscope, and capture images of the fluorescence in a field of view which is different from that of Example 1. Subsequently, the inventors perform the bleaching treatment on the control slide by irradiating the control slide with a laser beam with a wavelength of 640 nm at a power density of 470 W/cm$^2$ for two minutes. After the blocking treatment, the inventors capture images of the fluorescence on the same field of view again.

EXAMPLE 3

On the field of view used to make the observation in Example 2, the inventors capture images of the fluorescence again after the primary antibody treatment.

COMPARATIVE EXAMPLE 1

Before the activation treatment process, the inventors drop Reaction Buffer onto the control slide, and seal the control slide with a cover glass. Thereafter, the inventors set the control slide in the fluorescence microscope, and capture images of the fluorescence in a field of view which is different from those of Examples 1 to 3. Subsequently, the inventors perform the bleaching treatment on the control slide by irradiating the control slide with a laser beam with a wavelength of 640 nm at a power density of 470 W/cm$^2$ for two minutes. After the activation treatment, the inventors capture images of the fluorescence on the same field of view again.

COMPARATIVE EXAMPLE 2

On the field of view used to capture the images of the fluorescence in Example 1, the inventors capture images of the fluorescence again after the DNA denaturation treatment.

The fluorescence microscope used to capture the images in Examples 1 to 3 as well as Comparative Examples 1 and 2 does not include the phase plate 110 illustrated in FIG. 3.

[Result of Examination]

FIG. 6A is a diagram illustrating a result of the examination concerning Comparative Example 1. A left-end image in FIG. 6A is a captured image obtained by capturing an image of the control slide after performing the deparaffinization treatment process on the human breast cancer cell on the control slide, but before performing the activation treatment process on the human breast cancer cell thereon. As illustrated in the left-end image in FIG. 6A, the image captures the autofluorescence from the breast cancer cell after the deparaffinization treatment. White-shining parts of the captured image represent the autofluorescence.

A center image in FIG. 6A is an image captured after performing the bleaching treatment by, as described above, irradiating the control slide with the laser beam with the wavelength of 640 nm. The image-capturing field of view is the same as that which is used to capture the left-end image in FIG. 6A. An area surrounded by a white broken circle is irradiated with the laser beam. As learned from the center image in FIG. 6A, the bleaching treatment inhibits the autofluorescence.

A right-end image in FIG. 6A is an image captured after further performing the activation treatment on the control slide which follows the bleaching treatment. This captured image corresponds to a result of the examination concerning Comparative Example 1. The image-capturing field of view is the same as that which is used to capture the left-end and center images in FIG. 6A. As learned from the right-end image in FIG. 6A, the inventors observe that the activation treatment makes the autofluorescence recover.

FIG. 6B is a diagram illustrating results of the examinations concerning Example 1 and Comparative Example 2. The image-capturing field of view used in the case illustrated in FIG. 6B is different from that which is used in the case illustrated in FIG. 6A. A left-end image in FIG. 6B is a captured image obtained by capturing an image of the control slide after performing the activation treatment process on the human breast cancer cell on the control slide, but before performing the protease treatment process. As illustrated in the left-end image in FIG. 6B, the image captures the autofluorescence from the breast cancer cell after the activation treatment. Whitish-shining parts of the captured image represent the autofluorescence.

An image second from the left in FIG. 6B is an image captured after performing the bleaching treatment on the control slide by, as described above, irradiating the control slide with the laser beam with the wavelength of 640 nm. The image-capturing field of view is the same as that which is used to capture the left-end captured image in FIG. 6B. An area surrounded by a white broken circle is irradiated with the laser beam. As learned from the image second from the left in FIG. 6B, the bleaching treatment inhibits the autofluorescence.

An image third from the left in FIG. 6B is an image captured after further performing the protease treatment process on the control slide which follows the bleaching process. This captured image corresponds to a result of the examination concerning Example 1. The image-capturing field of view is the same as that which is used to capture the left-end image and the image second from the left in FIG. 6B. As learned from the image third from the left in FIG. 6B, the inventors observe that despite performing the protease treatment process, almost no autofluorescence recovers.

A right-end image in FIG. 6B is an image captured after further performing the DNA denaturation treatment process on the control slide. This captured image corresponds to a result of the examination concerning Comparative Example 2. The image-capturing field of view is the same as that which is used to capture the other captured images in FIG. 6B. As learned from the right-end image in FIG. 6B, the inventors observe that the DNA denaturation treatment process makes the autofluorescence recover.

FIG. 6C is a diagram illustrating results of the examinations concerning Example 2 and Example 3. The image-capturing field of view used in the case illustrated in FIG. 6C is different from those which are used in the cases illustrated in FIGS. 6A and 6B. A left-end image in FIG. 6C is a captured image obtained by capturing an image of the control slide after performing the DNA denaturation treatment process on the human breast cancer cell on the control slide, but before performing the blocking treatment process. As illustrated in the left-end image in FIG. 6C, the image captures the autofluorescence from the breast cancer cell after the DNA denaturation treatment. White-shining parts of the captured image represent the autofluorescence.

An image second from the left in FIG. 6C is an image captured after performing the bleaching treatment on the control slide by, as described above, irradiating the control slide with the laser beam with the wavelength of 640 nm. The image-capturing field of view is the same as that which is used to capture the left-end captured image in FIG. 6C. An area surrounded by a white broken circle is irradiated with the laser beam. As learned from the image second from the left in FIG. 6C, the bleaching treatment inhibits the autofluorescence.

An image third from the left in FIG. 6C is an image captured after further performing the blocking treatment process on the control slide which follows the bleaching process. This captured image corresponds to a result of the examination concerning Example 2. The image-capturing field of view is the same as that which is used to capture the left-end image and the image second from the left in FIG. 6C. As learned from the image third from the left in FIG. 6C, the inventors observe that despite performing the blocking treatment process, almost no autofluorescence recovers.

A right-end image in FIG. 6C is an image captured after further performing the primary antibody treatment process on the control slide. This captured image corresponds to a result of the examination concerning Example 3. The image-capturing field of view is the same as that which is used to capture the other captured images in FIG. 6C. As learned from the right-end image in FIG. 6C, the inventors observe that despite performing the primary antibody treatment process, almost no autofluorescence recovers.

FIG. 7 is a table for summarizing the results of the foregoing examinations. For each of Examples 1 to 3 as well as Comparative Examples 1 and 2, the inventors perform processes marked with a circle, and capture the image after performing the last one of the processes marked with a circle. For each of Examples 1 to 3 as well as Comparative Examples 1 and 2, the inventors indicate the level of the recovery of the autofluorescence with the number of + (plus) marks in the lowermost row of the table based on the captured image. A single + (plus) mark means that almost no autofluorescence recovers. A larger number of + (plus) marks means that the level of the recovery of the autofluorescence is higher. The column under the "temperature" shows the temperatures at which the inventors heat the control slide in each process.

In Example 1, although the inventors perform the protease treatment process at a heating temperature of 37° C. after the bleaching process, almost no autofluorescence recovers. In Example 2, although the inventors perform the blocking treatment process at the heating temperature of 37° C. after the bleaching process, almost no autofluorescence recovers. In Example, 3, although the inventors perform the blocking treatment process at the heating temperature of 37° C. and further perform the primary antibody treatment at the heating temperature of 37° C. after the bleaching process, almost no autofluorescence recovers.

These results of the examinations confirm that even though the inventors perform the treatment process(es) at the heating temperature of 37° C. or less after the bleaching treatment process, almost no autofluorescence recovers after the bleaching process inhibits the autofluorescence. In other words, one may consider that after the bleaching treatment inhibits the autofluorescence, almost no autofluorescence recovers unless the treatment process(es) to be performed after the bleaching treatment process is carried out by raising the heating temperature beyond at least 37° C. The treatment processes illustrated in FIG. 1 or the pretreatment processes performed in the foregoing examinations do not include any treatment process to be performed by raising the temperature of the measurement specimen beyond 37° C. between the bleaching process and the image capture process. For this reason, one may consider that after the bleaching treatment inhibits the autofluorescence, almost no autofluorescence recovers during the image capture process.

In Comparative Example 1, the autofluorescence recovers to a large extent since the inventors perform the activation treatment process at a heating temperature of 90° C. after the bleaching process. In Comparative Example 2, the autofluorescence more obviously recovers since the inventors perform the protease treatment process at a heating temperature of 37° C. and further perform the DNA denaturation treatment process at heating temperatures of 95° C., 44° C. and 62° C. after the bleaching process. A comparison between Comparative Example 2 and Example 1 makes it clear that a cause of the obvious recovery of the autofluorescence in Comparative Example 2 is the DNA denaturation treatment process since unlike Example 1, Comparative Example 2 includes the DNA denaturation treatment process. However, the result of the examination concerning Comparative Example 2 does not clarify what heating temperature among 95° C., 44° C. and 62° C. is the cause of the recovery of the autofluorescence. For this reason, the results of the examinations concerning Comparative Examples 1 and 2 only makes it clear that after inhibited by the bleaching treatment, the autofluorescence recovers to a large extent when performing the treatment process by raising the heating temperature to at least 90° C. or higher after the bleaching treatment process.

<Examination 2>

Examination 2 examines a relationship between heating temperatures and levels of recovery of the autofluorescence. In Examination 2, the inventors keep the temperatures of the control slides at respective three different temperatures for the same length of time after performing the bleaching treatment on the control slides, and thereafter check the level of recovery of the autofluorescence for each control slide. In Examination 2, the inventors perform the bleaching treatment on each control slide after performing only the deparaffinization treatment process on the human breast cancer cell on the control slide. The inventors perform the bleaching treatment on each control slide by irradiating the control slide with light, which is obtained by regulating an amount of parallel beams using a field stop, for a certain length of time. Before and after the bleaching treatment, the inventors obtain captured images of the autofluorescence by capturing images of the autofluorescence using the fluorescence microscope. Subsequently, the inventors capture images of the autofluorescence using the fluorescence microscope again after keeping each control slide at a predetermined temperature for a certain length of time. The fluorescence microscope used to capture the images does not include phase plate 110 illustrated in FIG. 3.

Left-end images in FIGS. 8A to 8C are captured images obtained by capturing images of the control slides before the bleaching treatment using field of views which are different from one another, respectively. As illustrated in the left-end images in FIGS. 8A to 8C, the images each capture the autofluorescence from the breast cancer cell after the deparaffinization treatment. White-shining parts of the captured images represent the autofluorescence.

Center images in FIGS. 8A to 8C are images captured after performing the bleaching treatment by, as described above, irradiating the control slides with the laser beam with the wavelength of 640 nm. The image-capturing field of view used to capture these images is the same as those which is used to capture the left-end images in FIGS. 8A to 8C. Areas surrounded respectively by white broken circles are irradiated with the laser beam. As learned from the center images in FIGS. 8A to 8C, the bleaching treatment inhibits the autofluorescence.

A right-end image in FIG. 8A is a captured image obtained by capturing an image of the control slide after leaving the control slide at room temperature of 24° C. for 20 minutes following the bleaching treatment. The image-capturing field of view is the same as that which is used to capture the left-end and center images in FIG. 8A. A right-end image in FIG. 8B is a captured image obtained by capturing an image of the control slide after heating the control slide at a temperature of 44° C. for 20 minutes following the bleaching treatment. The image-capturing field of view is the same as that which is used to capture the left-end and center images in FIG. 8B. A right-end image in FIG. 8C is a captured image obtained by capturing an image of the control slide after heating the control slide at a temperature of 62° C. for 20 minutes following the bleaching treatment. The image-capturing field of view is the same as that which is used to capture the left-end and center images in FIG. 8C.

From a comparison between the center and right-end captured images in FIG. 8A, the inventors can confirm that in the case where the inventors leave the control slide at room temperature of 24° C. following the bleaching treatment, almost no autofluorescence recovers after the bleaching treatment inhibits the autofluorescence. Similarly, from a comparison between the center and right-end captured images in FIG. 8B, the inventors can confirm that in the case where the inventors heat the control slide at the temperature of 44° C. following the bleaching treatment, almost no autofluorescence recovers after the bleaching treatment inhibits the autofluorescence. In contrast, from a comparison between the center and right-end captured images in FIG. 8C, the inventors can confirm that in the case where the inventors heat the control slide at the temperature of 62° C. following the bleaching treatment, the autofluorescence recovers after the bleaching treatment inhibits the autofluorescence.

Figure 9:
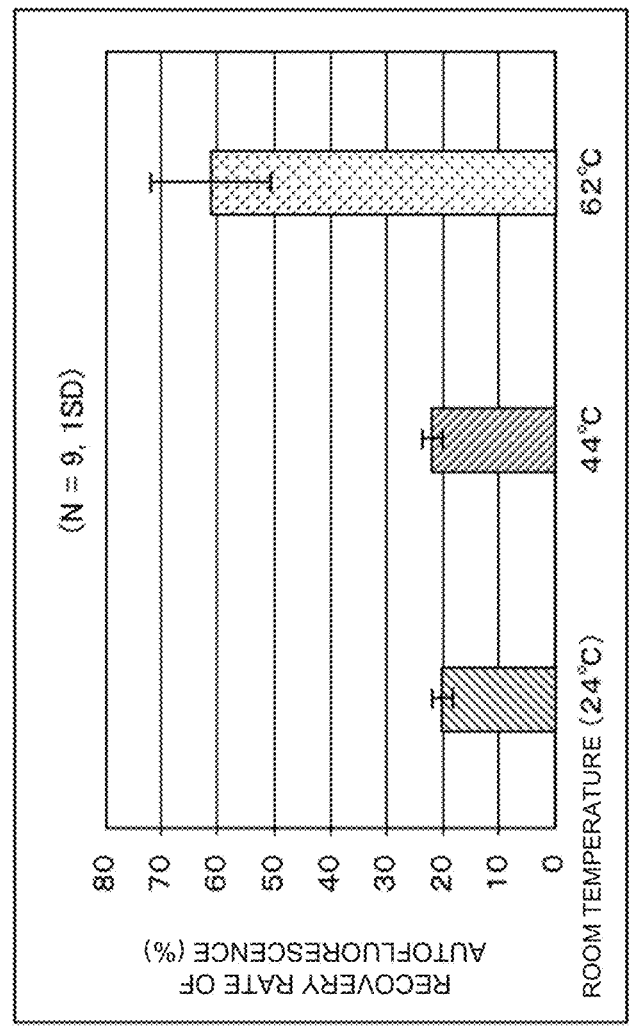
FIG. 9 is a table summarizing the results of Examination 1 of the embodiment.

FIG. 9 includes graphs each illustrating a calculation result of calculating a recovery rate of autofluorescence from a change in the state of the autofluorescence from the center image to the right-end image in each of FIGS. 8A to 8C on the basis of a brightness value of each image.

The inventors obtain the recovery rate of autofluorescence as follows. For example, in the case illustrated in FIG. 8A, the inventors obtain a brightness at an arbitrary position in a cell included in a broken circle in the left-end image captured before the bleaching treatment. The inventors further obtain a brightness at the same position in the center image captured after the bleaching treatment, and a brightness at the same position in the right-end image captured after keeping the temperature for the predetermined length of time. From the thus-obtained brightnesses, the inventors calculate the recovery rate of autofluorescence at the same position using the following expression.

Recovery Rate of Autofluorescence=(Brightness after Keeping Temperature−Brightness after Bleaching)/(Brightness before Bleaching−Brightness after Bleaching)×100    (1)

Similarly, the inventors calculate the recovery rate of autofluorescence at each of 8 different positions included in the same broken circle. The inventors obtain an average and a standard deviation of the recovery rates of autofluorescence at the 9 respective positions. Furthermore, for each of the cases illustrated in FIGS. 8B and 8C, the inventors obtain an average and a standard deviation of the recovery rates of autofluorescence at the 9 respective positions using the same method.

In FIG. 9, the graphs for "Room Temperature (24° C.)," "44° C." and "62° C." represent the recovery rates of autofluorescence for the captured images illustrated in FIGS. 8A to 8C. The inventors show a bar representing the standard deviation of the recovery rates of autofluorescence in a top portion of each graph. From the graphs in FIG. 9, it is learned that in the case of FIG. 8A where the inventors leave the control slide under an environment at room temperature of 24° C. after the bleaching treatment, the recovery rate of autofluorescence is approximately 20%, and that almost no autofluorescence recovers. It is further learned that in the case of FIG. 8B where the inventors heat the control slide at the temperature of 44° C. after the bleaching treatment, the recovery rate of autofluorescence is slightly higher than 20%, and that almost no autofluorescence recovers. In contrast, it is learned that in the case of FIG. 8C where the inventors heat the control slide at the temperature of 62° C. after the bleaching treatment, the recovery rate of autofluorescence exceeds 60%, and that the autofluorescence recovers to a large extent.

The results of the examinations illustrated in FIGS. 8A to 8C and FIG. 9 make it clear that in a case where at least the treatment process in which the heating temperature is raised to 62° C. or higher is performed after the bleaching treatment process, the autofluorescence recovers to a large extent after the bleaching treatment inhibits the autofluorescence. For this reason, it is necessary that the pretreatment process does not include at least the treatment process in which the heating temperature is raised to 62° C. or higher after the bleaching treatment process. This makes it possible to avoid the recovery of the autofluorescence during the image capture after the bleaching process inhibits the autofluorescence.

The results of the examinations illustrated in FIGS. 8A to 8C and FIG. 9 make it clear that even if the treatment process is performed at the heating temperature of 44° C. after the bleaching treatment process, the autofluorescence does not recover so much. In other words, one may consider that after the bleaching treatment inhibits the autofluorescence, almost no autofluorescence recovers unless the treatment process to be performed after the bleaching process is carried out by raising the heating temperature beyond at least 44° C. The treatment processes illustrated in FIG. 1 or the pretreatment process performed in the foregoing examinations does not include any treatment process to be performed by raising the temperature of the measurement specimen beyond 44° C. between the bleaching process and the image capture process. This makes it possible to securely avoid the recovery of the autofluorescence during the image capture after the bleaching process inhibits the autofluorescence.

<Examination 3>

Examination 3 examines how the level at which to detect fluorescence from fluorescent dyes differ between the analysis process with the bleaching treatment performed in the pretreatment process and the analysis process with no bleaching treatment performed in the pretreatment process.

[Pretreatment Process]

In Examination 3, too, the inventors perform the above-described pretreatment process. In Examination 3, before the secondary antibody treatment process, the inventors set a control slide in a microscope, and perform the bleaching treatment on the control slide using three manipulations. To put it concretely, in Manipulation 1, the inventors irradiate the control slide with a laser beam with a wavelength of 405 nm at a power density of 130 W/cm$^2$ for two minutes; in Manipulation 2, the inventors irradiate the control slide with a laser beam with a wavelength of 514 nm at a power density of 200 W/cm$^2$ for two minutes; and in Manipulation 3, the inventors irradiate the control slide with a laser beam with a wavelength of 640 nm at a power density of 1100 W/cm$^2$ for 10 minutes. The inventors emit the laser beams to three mutually-different fields of view for the respective manipulations.

[Image Capture Preparation Process]

The inventors drop 50 μL of a mount medium with the following composition onto the control slide prepared in the pretreatment process, cover the control glass, and fix the cover glass to the control glass with manicure.

| 1M Tris (pH 7.5) | 5 μL |
|---|---|
| 1M NaCl | 1 μL |
| 25% glucose | 40 μL |
| 2-mercaptoethanol | 1 μL |
| 5000 U/mL Glucose Oxidase | 1 μL |
| 1000 μg/mL catalase | 1 μL |
| H2O5 | 1 μL |

[Image Capture Process]

The inventors set the control slide prepared in the image capture preparation process in the microscope, and obtain 500 images of the fluorescence from the parts of the control slide which are irradiated with the respective laser beams in the bleaching treatment, while irradiating the parts of the control slide with the laser beam with the wavelength of 640 nm for an exposure time of 15 msec. The inventors set the power intensity of the laser beam for the exposure at 690 W/cm2. Incidentally, the inventors obtain the images of the fluorescence by capturing the images thereof under a condition in which: as in the case of image capture section 100 illustrated in FIG. 3, a phase plate is set between the mirror body of the microscope and the fluorescence detection camera; and the phase plate divides the fluorescence into two beams of fluorescence.

[Analysis Process]

Using the last one of the 500 images captured in the image capture process, the inventors calculate a standard deviation of fluorescence intensities in each of 9 cells as follows. First of all, the inventors arbitrarily select 3 cells from the cells which are present at the center of one of the three fields of view in the captured image. Subsequently, the inventors circle an arbitrary area inside each of the nuclei of the 3 arbitrary cells. After that, the inventors obtain a standard deviation of fluorescence intensities in the circled arbitrary area inside the nucleus. By repeating this procedure, the inventors obtain a standard deviation of fluorescence intensities from each of the three cells. Then, the inventors perform this work on the other two fields of view in which the control slide is irradiated with the respective laser beams in the bleaching treatment process. Thereby, the inventors obtain the standard deviations respectively from the 9 cells in total. Subsequently, the inventors calculate an average and a standard deviation of the 9 standard deviations.

[Comparative Example]

The inventors obtain 500 images of the fluorescence from parts of the control slide, which are not irradiated with the laser beams in Manipulations 1 to 3, while irradiating the parts of the control slide with the laser beam with the wavelength of 640 nm for an exposure time of 15 msec. The inventors set the power intensity of the laser beam for the exposure at 690 W/cm2. In this case, too, the inventors use the phase plate to capture the images.

For each of Manipulations 1 to 3, the inventors perform the same analysis process as described above. Thereby, the inventors obtain a standard deviation of fluorescence intensities from each of the nuclei of 9 arbitrary cells. Thereafter, the inventors calculate an average and a standard deviation of the 9 obtained standard deviations.

[Result of Examination]

Figure 10A:
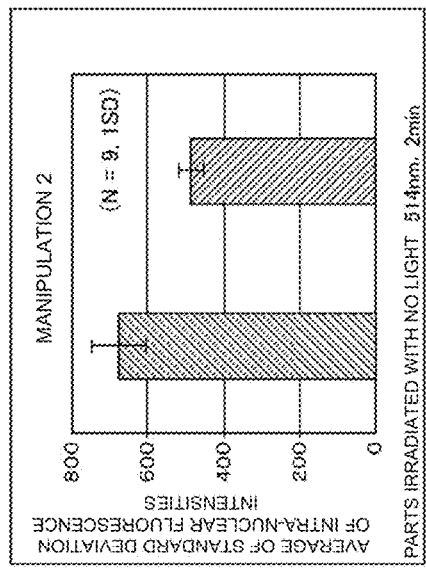
FIGS. 10A to 10C illustrate graphs obtained in Examination 3 of the embodiment, and each represent a comparison in a level of detection between a fluorescent dye in the case of performing the bleaching treatment using a beam of light while changing the wavelength of the beam of light for each of Manipulations 1 to 3, and a fluorescent dye in the case of not performing such bleaching treatment.

In FIG. 10A, a graph on the right represents the average of the standard deviation of intra-nuclear fluorescence intensities obtained from the part irradiated with the laser beam in Manipulation 1, while a graph on the left represents the average of the standard deviation of intra-nuclear fluorescence intensities obtained from the parts not irradiated with the laser beam in Manipulation 1. FIG. 10A shows a bar representing the standard deviation of intra-nuclear fluorescence intensities in a top portion of each graph. In Manipulation 1, the average of the standard deviations is lower in the part irradiated with the laser beam in the bleaching treatment than in the parts not irradiated with the laser beam in the bleaching treatment. In other words, it is clear that the part irradiated with the laser beam has less variation in the fluorescence intensities and results in detection of the better-separated fluorescence from the fluorescent dyes than the parts not irradiated with the laser beam.

Figure 10B:
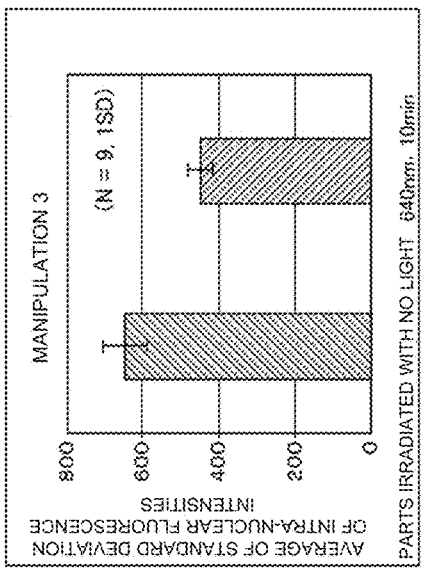
Figure 10C:
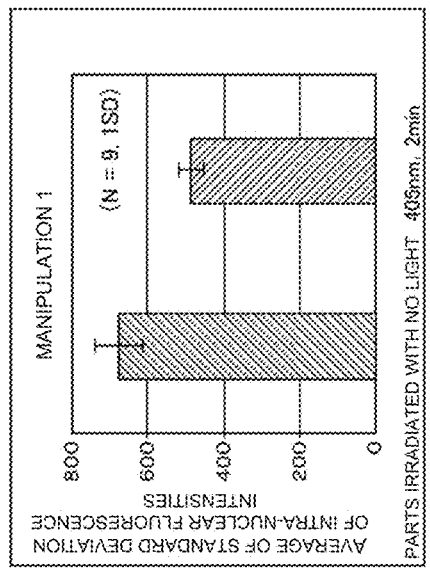

FIGS. 10B and 10C illustrate graphs representing results of examinations on Manipulations 2 and 3 in the same manner as FIG. 10A. As illustrated in FIGS. 10B and 10C, in Manipulations 2 and 3, too, the average of the standard deviations is lower in the part irradiated with the laser beam in the bleaching treatment than in the parts not irradiated with the laser beam in the bleaching treatment. In other words, it is clear that the part irradiated with the laser beam has less variation in the fluorescence intensities and results in detection of the better-separated fluorescence from the fluorescent dyes than in the parts not irradiated with the laser beam.

From Examination 3, the inventors confirm that the performing of the bleaching treatment with the laser beam irradiation can enhance the level at which to detect the fluorescence from the fluorescent dyes. FIGS. 10A to 10C show that the level at which to detect the fluorescence from the fluorescent dyes is almost the same among Manipulations 1 to 3. This clarifies that as the wavelength of the beam of light emitted in the bleaching treatment becomes shorter, the beam of light can inhibit the autofluorescence at lower power intensity for a shorter irradiation time. From this, it is desirable that a beam of light with a shorter wavelength be used to perform the bleaching treatment quickly and efficiently.

It should be noted that the bleaching treatment can be performed using a reagent instead of light. For example, a reagent for inhibiting autofluorescence of lipofuscin may be used. However, the use of light for the bleaching treatment in the above-described manner makes it possible to easily perform the bleaching treatment, since the bleaching treatment can be achieved by only emitting the light for a predetermined length of time. Particularly, the use of a laser beam with a short wavelength enables the bleaching treatment to be performed at low power intensity for a short length of time.

<Examination 4>

Examination 4 examines how the autofluorescence influences the fluorescence of the fluorescent dyes.

[Pretreatment Process and Image Capture Preparation Process]

In Examination 4, too, the inventors perform the above-described pretreatment process. In Examination 4, before the secondary antibody treatment process, the inventors set a control slide in a microscope, and perform the bleaching treatment on the control slide by irradiating the control slide with a laser beam with a wavelength of 514 at a power intensity of 200 W/cm² for 5 minutes. The inventors perform the image capture process in the same manner as Examination 3 described above.

[Image Capture Process]

The inventors set the control slide prepared in the image capture preparation process in the microscope, and irradiate a part of the control slide, which is irradiated with the laser beam in the bleaching treatment, with a laser beam with a wavelength of 640 nm at a power intensity of 690 W/cm² for 5 seconds. Thereafter, the inventors obtain 30 images of the fluorescence from the part of the control slide while irradiating the part of the control slide with the laser beam with the wavelength of 640 nm at a power intensity of 690 W/cm² for an exposure time of 15 msec. Incidentally, the inventors obtain the images of the fluorescence by capturing the images thereof under a condition in which: as in the case of image capture section 100 illustrated in FIG. 3, a phase plate is set between the mirror body of the microscope and the fluorescence detection camera; and the phase plate divides the fluorescence into two beams of fluorescence.

[Comparative Example]

The inventors also irradiate apart of the control slide, which is not irradiated with the laser beam in the bleaching treatment, with the laser beam with the wavelength of 640 nm at the power intensity of 690 W/cm² for 5 seconds. Thereafter, the inventors obtain 30 images of the fluorescence from the part of the control slide, which is not irradiated with the laser beam in the bleaching treatment, while irradiating the part of the control slide with the laser beam with the wavelength of 640 nm at the power intensity of 690 W/cm² for an exposure time of 15 msec. In this case, too, the inventors use the phase plate to capture the images.

[Result of Examination]

Figure 11B:
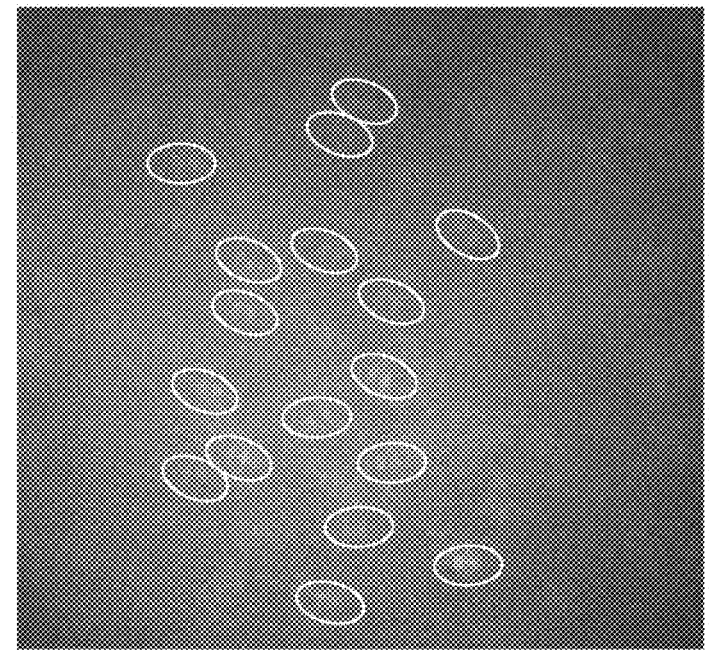
FIG. 11B is a captured image obtained in Examination 3 of the embodiment by capturing an image of the fluorescence from the test substance with no autofluorescence from the measurement specimen inhibited.
Figure 11A:
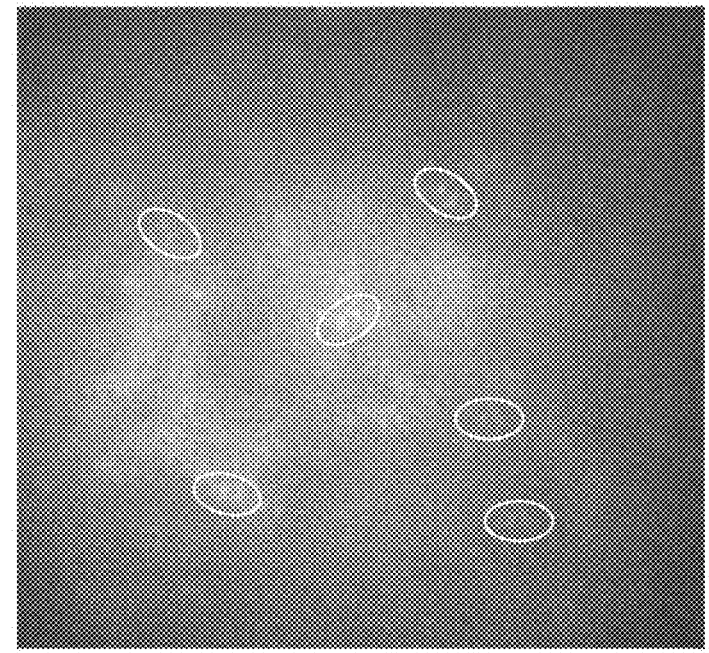
FIG. 11A is a captured image obtained in Examination 3 of the embodiment by capturing an image of fluorescence from the test substance with the autofluorescence from the measurement specimen inhibited by the bleaching treatment.

FIGS. 11A and 11B respectively illustrate a captured image obtained with the bleaching treatment performed, and a captured image obtained with no bleaching treatment performed. FIGS. 11A and 11B add white circles each for indicating a pair of luminescent spots to the captured images.

As illustrated in FIG. 11A, the inventors can observe pairs of luminescent spots in areas circled in white on the captured image of the part in the case of performing the bleaching treatment. The number of pairs of observable luminescent spots is 17. In contrast, from FIG. 11B, the inventors can observe only 6 pairs of luminescent spots because of the influence of the autofluorescence from the cells. The result of this examination makes it clear that the performing of the bleaching treatment makes it possible to satisfactorily detect the fluorescence from the fluorescent dyes even in the case where the phase plate divides the fluorescence emitted from each fluorescent dye into two beams of fluorescence.

3. Sample Analyzer

Figure 12:
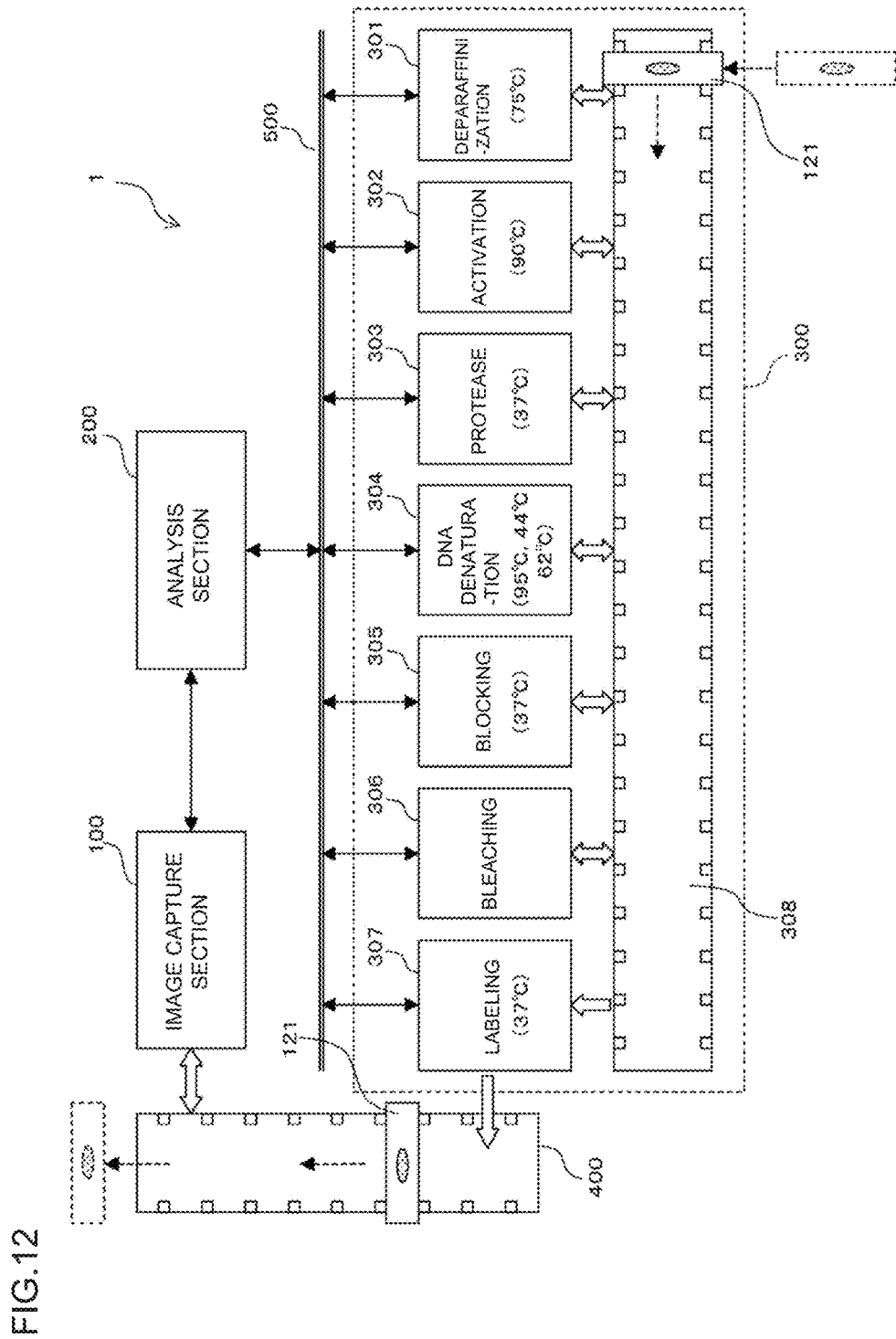
FIG. 12 is a diagram illustrating a configuration of a sample analyzer according to the embodiment.

Based on the results of the examinations, one may configure sample analyzer 1 as illustrated in FIG. 12, for example.

As illustrated in FIG. 12, sample analyzer 1 includes pretreatment section 300, conveyor 400 and data bus 500 in addition to image capture section 100 and analysis section 200 which are described above. Image capture section 100 and analysis section 200 have their respective configurations illustrated in FIG. 3, and respectively perform the image capture process in FIG. 4B and the analysis process in FIG. 5A. As described above, image capture section 100 captures images of the measurement specimen which pretreatment section 300 pretreats. Analysis section 200 extracts the test substance by, as described above, processing the captured images obtained by image capture section 100.

Pretreatment section 300 pretreats the measurement specimen in order to capture the images of the test substance. Pretreatment section 300 performs the treatments in step S11 to S17 and the treatment in step S21 which FIG. 1 illustrates. Incidentally, in FIG. 12, pretreatment section 300 is configured to perform the bleaching process in step S21 in FIG. 1 after the blocking treatment process in step S15 in FIG. 1. Nevertheless, the bleaching process may be placed anywhere after the step S15 in FIG. 1. For example, pretreatment section 300 may perform the bleaching process between steps S16 and S17. In pretreatment section 300, too, the location of the treatment unit configured to perform the bleaching process can be changed depending on the necessity.

Pretreatment section 300 includes 7 treatment units 301 to 307 and conveyor 308. Conveyor 308 sequentially conveys slide glass 121 with the measurement specimen placed thereon to the fronts of treatment units 301 to 307. Conveyor 308 conveys slide glass 121 in a leftward direction only. Each of treatment units 301 to 306 takes slide glass 121 therein from conveyor 308 and processes slide glass 121, when conveyor 308 conveys slide glass 121 to the front of the treatment unit. After the process, the treatment unit returns slide glass 121 onto conveyor 308. Treatment unit 307 takes slide glass 121 therein from conveyor 308 and processes slide glass 121, when conveyor 308 conveys slide glass 121 to the front of treatment unit 307. After the process, treatment unit 307 send out slide glass 121 onto conveyor 400 disposed in the left of treatment unit 307.

Treatment units 301 to 305 perform the treatments insteps S11 to S15 in FIG. 1, respectively. To put it concretely, treatment units 301 to 305 perform the deparaffinization treatment, the activation treatment, the protease treatment, the DNA denaturation treatment and the blocking treatment on the measurement specimen on slide glass 121, respectively.

Treatment unit 306 performs the treatment in step S21 in FIG. 1. To put it concretely, treatment unit 306 performs the bleaching treatment on the measurement specimen on slide glass 121 by irradiating the measurement specimen with light. Treatment unit 306 may include, for example, a laser light source; a collimator lens configured to convert light emitted from the laser light source into parallel beams; and a stop configured to regulate an amount of light which the collimator lens transmit, and to emit the resultant light onto the measurement specimen. Treatment unit 306 is capable of easily performing the bleaching treatment since treatment unit 306 is configured to perform the bleaching treatment using the light in this manner.

Treatment unit 307 performs the treatments in steps S16 and S17 in FIG. 1. To put it concretely, treatment unit 307 performs the treatment for binding the primary antibody to the DNP-labeled nucleic acid probe bound to the test substance in the measurement specimen, and the treatment for further binding the fluorescent dye, or the fluorescence-labeled secondary antibody, to the primary antibody bound to the DNP-labeled nucleic acid probe. Treatment units 301 to 307 and conveyor 308 are connected to analysis section 200 via data bus 500. Analysis section 200 controls treatment units 301 to 307 and conveyor 308. Treatment units 301 to 307 and conveyor 308 each include a detector, such as a sensor, configured to detect the arrival of slide glass 121 at a predetermined position.

After performing the labeling treatment on slide glass 121, treatment unit 307 sends out slide glass 121 onto conveyor 400 disposed in the left of treatment unit 307. Conveyor 400 conveys slide glass 121 to the front of image capture section 100. Image capture section 100 takes slide glass 121 therein from conveyor 400, and captures images. After capturing the images, image capture section 100 returns slide glass 121 onto conveyor 400. Conveyor 400 conveys slide glass 121, which the image capture section 100 returns onto conveyor 400, to a collection unit. Analysis section 200 controls conveyor 400 as well. Conveyor 400 includes a detector, such as a sensor, configured to detect the arrival of slide glass 121 at a predetermined position.

It should be noted that treatment units 301 to 307 do not have to be provided as the units separate from one another. Treatment units 301 to 307 may be integrated into a single unit or system so that the treatments by the respective treatment units are performed inside the single unit or system. Furthermore, pretreatment section 300 and image capture section 100 may be integrated into a single unit.

In pretreatment section 300 of sample analyzer 1 illustrated in FIG. 12, treatment unit 306 configured to perform the bleaching treatment is arranged downstream, in treatment order, of treatment unit 304 configured to treat the measurement specimen by raising the temperature of the measurement specimen to 62° C. or higher. Treatment unit 304 configured to perform the DNA denaturation treatment for denaturing DNA by heating the measurement specimen treats the measurement specimen before treatment unit 306 configured to perform the bleaching treatment. Treatment unit 301 configured to perform the deparaffinization treatment and treatment unit 302 configured to perform the activation treatment also treat the measurement specimen before treatment unit 306 configured to perform the bleaching treatment. Moreover, pretreatment section 300 does not include any treatment unit configured to treat the measurement specimen by heating the measurement specimen at 62° C. or higher in a part downstream of treatment unit 306 configured to perform the bleaching treatment. For these reasons, pretreatment section 300 provides the measurement specimen to image capture section 100 with the autofluorescence from the measurement specimen securely inhibited as shown by the foregoing examinations. This makes it possible for image capture section 100 to capture images of the fluorescence from the fluorescent dye bound to the test substance with the autofluorescence from the measurement specimen inhibited. Analysis section 200 is capable of accurately detecting the fluorescence from the bound dye, since analysis section 200 analyzes the captured images in which the autofluorescence is inhibited. Accordingly, analysis section 200 is capable of analyzing the test substance included in the measurement specimen with high accuracy.

In sample analyzer 1 illustrated in FIG. 12, pretreatment section 300 include neither a treatment unit configured to treat the measurement specimen by heating the measurement specimen at 44° C. or higher nor a treatment unit configured to treat the measurement specimen by heating the measurement specimen beyond 37° C. in the part downstream of treatment unit 306 configured to perform the bleaching treatment. For this reason, pretreatment section 300 provides the measurement specimen to image capture section 100 with the autofluorescence from the measurement specimen more securely inhibited as shown by the foregoing examinations. This makes it possible for image capture section 100 to capture images of the fluorescence from the fluorescent dye bound to the test substance with the autofluorescence from the measurement specimen inhibited more. Analysis section 200 is capable of more accurately detecting the fluorescence from the bound dye, since analysis section 200 analyzes the captured images in which the autofluorescence is securely inhibited. Accordingly, analysis section 200 is capable of analyzing the test substance included in the measurement specimen with higher accuracy.

The invention is applicable to a sample analyzing method and a sample analyzer of analyzing a test substance other than HER2 gene and CEP 17. In addition, the invention is also usable to diagnose a disease apart from the breast cancer screening. The invention is applicable to a sample analyzing method and a sample analyzer of analyzing a frozen tissue, a living cell and the like. Besides, the invention is applicable to the inhibition of autofluorescence from a magnetic bead used in a digital PCR.

HER2 gene which is a prognostic factor of breast cancer is known as a specific gene whose amplification arises with progress in the condition of the disease. The inventors of this application try to inhibit autofluorescence using the method disclosed in US Patent Application Publication No. US2010/0120060A1 when analyzing a breast cancer cell in a measurement specimen made of a xenograft simulating breast cancer taken from a diseased tissue of a subject. However, the inventors cannot effectively inhibit the autofluorescence from the measurement specimen, and accordingly cannot accurately detect the fluorescence originated from the fluorescent dye.

The embodiments explained above can effectively inhibit autofluorescence which intrinsically arises from a measurement specimen, and can accurately detect fluorescence from a fluorescent dye bound to a specific substance.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A sample analyzing method comprising:
   denaturing DNA by heating a measurement specimen so that a temperature of the measurement specimen is raised to 62° C. or higher;
   bleaching the measurement specimen to inhibit autofluorescence from the measurement specimen;
   labeling a test substance by binding a fluorescent dye to the test substance in the measurement specimen; and
   capturing an image of fluorescence originated from the fluorescent dye by irradiating the measurement specimen with light, wherein
   the denaturing of the DNA is performed before the bleaching,
   the labeling and the capturing of the image are performed after the bleaching, and
   a temperature of the measurement specimen during an entirety of the bleaching, the labeling and the capturing of the image is lower than 62° C. to inhibit a recovery of the autofluorescence.

2. The sample analyzing method according to claim 1, further comprising activating the measurement specimen, wherein the activating is performed before the bleaching.

3. The sample analyzing method according to claim 1, further comprising deparaffinizing the measurement specimen, wherein
   the deparaffinizing is performed before the bleaching.

4. The sample analyzing method according to claim 1, wherein the bleaching inhibits the autofluorescence originated from the measurement specimen by irradiating the measurement specimen with light.

5. The sample analyzing method according to claim 1, further comprising detecting the test substance by processing the captured image obtained in the capturing of the image.

6. The sample analyzing method according to claim 1, wherein
   the measurement specimen is a cell taken from a diseased tissue of a breast cancer, and
   the test substance comprises an HER2 gene.

7. The sample analyzing method according to claim 1, wherein
   the fluorescent dye is switchable between an activation condition in which the fluorescence is excited when the fluorescent dye is irradiated with light for excitation and an inactivation condition in which the fluorescence is not excited even when the fluorescent dye is irradiated with the light for excitation, and
   the capturing of the image includes
      quenching the fluorescence of the fluorescent dye,
      activating part of the fluorescent dye whose fluorescence is quenched, and
      capturing an image of the fluorescence by irradiating the measurement specimen with the light for excitation.

* * * * *